US012508146B2

(12) United States Patent
Hsu et al.

(10) Patent No.: US 12,508,146 B2
(45) Date of Patent: Dec. 30, 2025

(54) CERVICAL COLLAR

(71) Applicant: Ossur Iceland ehf, Reykjavik (IS)

(72) Inventors: Henry Hsu, Foothill Ranch, CA (US); Mark Harman Powell, Foothill Ranch, CA (US); Christopher Callicott Webster, Foothill Ranch, CA (US); Jared Olivo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 1164 days.

(21) Appl. No.: 17/193,754

(22) Filed: Mar. 5, 2021

(65) Prior Publication Data

US 2021/0186735 A1 Jun. 24, 2021

Related U.S. Application Data

(63) Continuation of application No. 15/697,021, filed on Sep. 6, 2017, now Pat. No. 10,945,872.

(Continued)

(51) Int. Cl.

*A61F 5/055* (2006.01)
*A61F 5/37* (2006.01)

(52) U.S. Cl.

CPC ................ *A61F 5/055* (2013.01); *A61F 5/37* (2013.01)

(58) Field of Classification Search

CPC ...... A61F 5/055; A61F 5/058; A61F 5/05808; A61F 5/37; A61F 7/00; A61F 5/3707;

(Continued)

(56) References Cited

U.S. PATENT DOCUMENTS 2,088,207 A 7/1937 Kaiser
2,102,069 A 12/1937 Hanicke (Continued)

FOREIGN PATENT DOCUMENTS

CN 1646071 A 7/2005
CN 2933343 Y 8/2007

(Continued)

OTHER PUBLICATIONS

Levangie et al., "Joint Structure and Function: A Comprehensive Analysis", Fourth Edition, Chapter 4: The Vertebral Column, 2005 F.A. Davis Company, Philadelphia, PA, pp. 161-164.

(Continued)

*Primary Examiner* — Alireza Nia
*Assistant Examiner* — Robin Han
(74) *Attorney, Agent, or Firm* — Workman Nydegger

(57) ABSTRACT

A cervical collar having an anterior component including a main support, an intermediate support pivotally connecting to the main support at a rear portion of the anterior component, and forming a frontal opening with the main support. An adjustment mechanism connects the main support to the intermediate support and locks a position of the intermediate support relative to the main support at a front portion of anterior component. The adjustment mechanism has an actuator for disengaging the main support from the intermediate support at the front portion and permits the intermediate support to pivot relative to the main support at the rear portion to vary a height of the frontal opening. A posterior component of the cervical collar is adapted to provide improved anterior-posterior and lateral occipital support.

19 Claims, 18 Drawing Sheets

Related U.S. Application Data

(60) Provisional application No. 62/504,121, filed on May 10, 2017, provisional application No. 62/430,258, filed on Dec. 5, 2016, provisional application No. 62/396,279, filed on Sep. 19, 2016.

(58) Field of Classification Search
CPC ........ A61F 5/04; A61F 5/01; A61F 5/042–05; A61F 5/05883; A61F 2007/0001–0003; A61F 2007/0009–0012; A61F 13/12; A61F 13/128; A61B 5/6822; A63B 23/025; A41D 13/0512; A41D 13/05; A61H 1/0218; A61H 1/0292; A61H 1/0296; A61H 1/02
See application file for complete search history.

(56) References Cited

U.S. PATENT DOCUMENTS 2,735,424 A 2/1956 Benjamin
2,791,999 A 5/1957 Bustamante
2,801,630 A 8/1957 Moore
2,806,471 A 9/1957 Breese
2,818,063 A 12/1957 Smith et al.
2,820,455 A 1/1958 Hall
2,911,970 A 11/1959 Bartels
D188,302 S 6/1960 Monfardini
3,024,784 A 3/1962 Monfardini
3,027,894 A 4/1962 Moore
3,042,027 A 7/1962 Monfardini
3,050,052 A 8/1962 Grassl
3,060,930 A 10/1962 Grassl
3,075,521 A 1/1963 Grassl
3,135,256 A 6/1964 Gruber
3,177,869 A 4/1965 Bartels
D203,018 S 11/1965 Helferich
3,285,243 A 11/1966 Yellin
3,285,244 A 11/1966 Cottrell
3,306,284 A 2/1967 Mckinley
3,313,297 A 4/1967 Applegate et al.
3,320,950 A 5/1967 Mcelvenny
3,504,667 A 4/1970 McFarlane
3,512,523 A 5/1970 Barnett
3,756,226 A 9/1973 Calabrese et al.
3,916,884 A 11/1975 Attenburrow
3,916,885 A 11/1975 Gaylord, Jr.
4,099,523 A 7/1978 Lowrey
4,173,973 A 11/1979 Hendricks
4,205,667 A 6/1980 Gaylord, Jr.
4,325,363 A 4/1982 Berkeley
4,401,111 A 8/1983 Blackstone
4,413,619 A 11/1983 Garth
D278,747 S 5/1985 Peach, Jr.
4,520,801 A 6/1985 Lerman
4,538,597 A 9/1985 Lerman
4,562,833 A 1/1986 Pujals, Jr.
4,582,051 A 4/1986 Greene et al.
4,628,913 A 12/1986 Lerman
4,643,174 A 2/1987 Horiuchi
4,677,969 A 7/1987 Calabrese
4,702,233 A 10/1987 Omicioli
4,708,129 A 11/1987 Pujals, Jr.
4,712,540 A 12/1987 Tucker et al.
4,732,144 A 3/1988 Cunanan
4,745,922 A 5/1988 Taylor
4,827,915 A 5/1989 Gorsen
4,854,306 A 8/1989 Pujals, Jr.
4,886,052 A 12/1989 Calabrese
4,940,043 A 7/1990 Burns et al.
4,955,368 A 9/1990 Heimann
4,987,891 A 1/1991 Gaylord, Jr. et al.
D314,623 S 2/1991 Calabrese et al.
5,005,563 A 4/1991 Veale
5,038,759 A 8/1991 Morgenstern
5,058,572 A 10/1991 Schmid et al.
5,060,637 A 10/1991 Schmid et al.
5,097,824 A 3/1992 Garth
5,156,588 A 10/1992 Marcune et al.
5,180,361 A 1/1993 Moore et al.
5,201,702 A 4/1993 Mars
5,215,517 A 6/1993 Stevenson et al.
5,230,698 A 7/1993 Garth
5,275,581 A 1/1994 Bender
5,302,170 A 4/1994 Tweardy
RE34,714 E 8/1994 Burns et al.
5,346,461 A 9/1994 Heinz et al.
5,366,438 A 11/1994 Martin, Sr.
5,385,535 A 1/1995 McGuinness
5,433,696 A 7/1995 Osti
5,437,612 A 8/1995 Moore et al.
5,437,617 A 8/1995 Heinz et al.
5,445,602 A 8/1995 Grim et al.
D368,527 S 4/1996 Brooke
D369,660 S 5/1996 Myoga
5,520,619 A 5/1996 Martin
RE35,290 E 7/1996 Druskoczi
5,588,957 A 12/1996 Martin, Sr.
5,593,382 A 1/1997 Rudy, Jr. et al.
5,622,529 A 4/1997 Calabrese
5,624,387 A 4/1997 McGuinness
D379,232 S 5/1997 Brooke
5,632,722 A * 5/1997 Tweardy ................ A61F 5/055
602/18
5,688,229 A 11/1997 Bauer
5,716,335 A 2/1998 Iglesias et al.
5,728,054 A 3/1998 Martin
D393,718 S 4/1998 Traut et al.
5,785,670 A 7/1998 Hiebert
5,788,658 A 8/1998 Islava
5,795,315 A 8/1998 Traut et al.
5,797,713 A 8/1998 Tweardy et al.
5,797,863 A 8/1998 Kohnke
RE35,940 E 10/1998 Heinz et al.
5,865,773 A 2/1999 Koledin
5,904,662 A 5/1999 Myoga
5,934,599 A 8/1999 Hammerslag
5,964,722 A 10/1999 Goralnik et al.
5,976,098 A 11/1999 Sereboff
5,993,403 A 11/1999 Martin
6,027,467 A 2/2000 Nakamura et al.
6,036,664 A 3/2000 Martin, Sr. et al.
D422,710 S 4/2000 Maynard
6,045,522 A 4/2000 Grober
6,045,523 A 4/2000 Donaldson
6,050,965 A 4/2000 Pillai
6,056,711 A 5/2000 Domamski et al.
6,058,517 A 5/2000 Hartunian
RE36,745 E 6/2000 Rudy, Jr. et al.
6,071,255 A 6/2000 Calabrese
6,071,256 A 6/2000 Lam
6,090,058 A 7/2000 Traut et al.
6,165,146 A 12/2000 Giebeler
6,183,501 B1 2/2001 Latham
6,202,953 B1 3/2001 Hammerslag
6,245,033 B1 6/2001 Martin
6,254,560 B1 7/2001 Tweardy et al.
6,289,558 B1 9/2001 Hammerslag
6,308,345 B1 10/2001 Williams, Jr.
6,315,746 B1 11/2001 Garth et al.
6,423,020 B1 7/2002 Koledin
6,458,090 B1 10/2002 Walpin
6,494,854 B1 12/2002 Visness et al.
D475,139 S 5/2003 Myoga
6,632,722 B2 10/2003 Fujiwara et al.
6,663,581 B1 12/2003 Calabrese
6,663,630 B2 12/2003 Farley et al.
6,726,643 B1 4/2004 Martin
6,733,469 B2 5/2004 Miyaji et al.
6,740,055 B2 5/2004 Dominguez
6,770,046 B2 8/2004 Hansen
6,872,188 B2 3/2005 Caille et al.
6,913,584 B2 7/2005 Rudy, Jr. et al.
6,921,376 B2 7/2005 Tweardy et al.
6,926,686 B2 8/2005 Cheatham

(56) References Cited

U.S. PATENT DOCUMENTS

| | | | |
|---|---|---|---|
| 7,018,351 B1 | 3/2006 | Iglesias et al. | |
| 7,041,073 B1 | 5/2006 | Patron | |
| 7,070,573 B2 | 7/2006 | Axelsson | |
| 7,090,652 B2 | 8/2006 | Santelli, Jr. | |
| 7,090,653 B2 | 8/2006 | Moeller | |
| 7,128,724 B2 | 10/2006 | Marsh | |
| 7,141,031 B2 | 11/2006 | Garth et al. | |
| 7,198,610 B2 | 4/2007 | Ingimundarson et al. | |
| D542,919 S | 5/2007 | Leatt | |
| 7,258,677 B2 | 8/2007 | Rudy, Jr. et al. | |
| D552,742 S | 10/2007 | Leatt | |
| 7,291,121 B2 | 11/2007 | Rudy, Jr. et al. | |
| 7,297,127 B2 | 11/2007 | Lee et al. | |
| 7,311,686 B1 | 12/2007 | Iglesias et al. | |
| 7,371,221 B1 | 5/2008 | Baker | |
| 7,371,222 B2 | 5/2008 | Heinz et al. | |
| 7,399,288 B2 | 7/2008 | Chao | |
| 7,442,176 B2 | 10/2008 | Cojbasic | |
| D609,815 S | 2/2010 | Patterson | |
| 7,674,234 B2 | 3/2010 | Calco et al. | |
| D616,555 S | 5/2010 | Thorgilsdottir et al. | |
| D616,996 S | 6/2010 | Thorgilsdottir et al. | |
| D616,997 S | 6/2010 | Thorgilsdottir et al. | |
| D617,907 S | 6/2010 | Waller | |
| 7,815,585 B2 | 10/2010 | Vollbrecht | |
| 7,846,117 B2 | 12/2010 | Leatt et al. | |
| D631,167 S | 1/2011 | Leatt et al. | |
| 7,878,995 B2 | 2/2011 | Harty | |
| 7,896,827 B2 | 3/2011 | Ingimundarson et al. | |
| 7,981,068 B2 | 7/2011 | Thorgilsdottir et al. | |
| D643,978 S | 8/2011 | Abajo Alonso et al. | |
| D644,331 S | 8/2011 | Sandhu | |
| D644,332 S | 8/2011 | Sandhu | |
| 7,992,261 B2 | 8/2011 | Hammerslag et al. | |
| D647,623 S | 10/2011 | Thorgilsdottir et al. | |
| D647,624 S | 10/2011 | Thorgilsdottir et al. | |
| 8,038,635 B2 | 10/2011 | Dellanno | |
| 8,038,636 B2 | 10/2011 | Thorgilsdottir et al. | |
| D659,842 S | 5/2012 | Donaldson et al. | |
| D662,597 S | 6/2012 | Chang | |
| 8,216,167 B2 | 7/2012 | Garth et al. | |
| D666,302 S | 8/2012 | Joseph | |
| 8,257,292 B2 | 9/2012 | Linares | |
| D692,568 S | 10/2013 | Chiang et al. | |
| 8,545,423 B2 | 10/2013 | Patron | |
| D693,014 S | 11/2013 | Chiang et al. | |
| 8,679,044 B2 | 3/2014 | Thorgilsdottir et al. | |
| 8,932,243 B2 | 1/2015 | Calabrese | |
| 9,132,027 B2 | 9/2015 | Calco | |
| D767,825 S | 9/2016 | Georgeson et al. | |
| 9,713,546 B2 | 7/2017 | Thorsteinsdottir et al. | |
| 2002/0138028 A1 | 9/2002 | Rudy, Jr. et al. | |
| 2002/0156408 A1 | 10/2002 | Cheatham | |
| 2002/0156409 A1 | 10/2002 | Lee et al. | |
| 2002/0169401 A1 | 11/2002 | Walpin | |
| 2002/0173737 A1 | 11/2002 | Miyaji et al. | |
| 2003/0055367 A1 | 3/2003 | Dominguez | |
| 2003/0060744 A1 | 3/2003 | Caille et al. | |
| 2003/0181838 A1 | 9/2003 | Garth | |
| 2004/0039318 A1 | 2/2004 | Santelli, Jr. | |
| 2005/0101896 A1 | 5/2005 | Calabrese | |
| 2007/0027418 A1 | 2/2007 | Calco et al. | |
| 2007/0073203 A1 | 3/2007 | Moenning et al. | |
| 2007/0270728 A1 | 11/2007 | Chao | |
| 2009/0247918 A1 | 10/2009 | Patron | |
| 2010/0137768 A1 | 6/2010 | Thorgilsdottir et al. | |
| 2010/0268139 A1 | 10/2010 | Garth | |
| 2010/0298748 A1 | 11/2010 | Rosenfeld et al. | |
| 2011/0034844 A1 | 2/2011 | Thorgilsdottir et al. | |
| 2011/0066094 A1* | 3/2011 | Thorgilsdottir ......... | A61F 5/055 602/18 |
| 2011/0224591 A1 | 9/2011 | Thorgilsdottir et al. | |
| 2012/0053499 A1 | 3/2012 | Donaldson et al. | |
| 2012/0130295 A1 | 5/2012 | Haider | |
| 2012/0165712 A1 | 6/2012 | Calabrese | |
| 2012/0291189 A1* | 11/2012 | Chambers ............... | A61F 5/055 2/468 |
| 2013/0060179 A1 | 3/2013 | Modglin | |
| 2013/0281899 A1 | 10/2013 | Suarez et al. | |
| 2013/0281900 A1 | 10/2013 | Suarez et al. | |
| 2013/0310722 A1 | 11/2013 | Thorsteinsdottir et al. | |
| 2014/0012172 A1 | 1/2014 | Calco | |
| 2014/0107551 A1 | 4/2014 | Modglin | |
| 2014/0323938 A1 | 10/2014 | Suarez et al. | |
| 2015/0216708 A1 | 8/2015 | Garth et al. | |
| 2016/0287424 A1 | 10/2016 | Webster et al. | |
| 2017/0246022 A1 | 8/2017 | Calco et al. | |
| 2018/0078400 A1 | 3/2018 | Hsu et al. | |
| 2022/0125615 A1* | 4/2022 | Maher ....................... | A61F 7/10 |

FOREIGN PATENT DOCUMENTS

| | | |
|---|---|---|
| CN | 201150587 Y | 11/2008 |
| CN | 201602923 U | 10/2010 |
| CN | 102227196 A | 10/2011 |
| CN | 202015274 U | 10/2011 |
| DE | 19547115 A1 | 6/1997 |
| DE | 19849302 A1 | 4/2000 |
| DE | 10057286 A1 | 5/2002 |
| EP | 1738724 A1 | 1/2007 |
| EP | 2653139 A1 | 10/2013 |
| EP | 2886088 A1 | 6/2015 |
| FR | 2814362 A1 | 3/2002 |
| GB | 2165157 A | 4/1986 |
| GB | 2453996 A | 4/2009 |
| JP | 2007-330808 A | 12/2007 |
| WO | 94/09728 A1 | 5/1994 |
| WO | 95/22304 A1 | 8/1995 |
| WO | 96/40018 A1 | 12/1996 |
| WO | 9843568 A1 | 10/1998 |
| WO | 2014102340 A1 | 7/2014 |

OTHER PUBLICATIONS

Hsu et al., AAOS Atlas of Orthoses and Assistive Devices, Mosby, Elsevier Fourth Edition, 2008, Philadelphia, PA, p. 117-122.

Product Information Sheet, Philadelphia Tracheotomy Collar, obtained from www.ossur.com, prior to Aug. 6, 2010, 1 page.

Product Information Sheet, Platazote Sheets, WBC Industries, obtained from www.wbcindustries.com prior to Aug. 6, 2010, 2 pages.

"Range-of-Motion Restriction and Craniofacial Tissue-Interface Pressure From Four Cervical Collars", The Journal of Trauma Injury, Infection, and Critical Care, vol. 63, No. 5, Nov. 2007, pp. 1120-1126.

"Ossur Is Immobilization", www.ossur.com, 2008, pp. 1-16.

"Miami J Patient Care Handbook", www.ossur.com, 2010, pp. 1-16.

Jacobson et al. "Improving Practice Efforts to Reduce Occipital Pressure Ulcers", Journal of Nursing Care Quality, vol. 23, No. 3, 2008, pp. 283-288.

Bell et al. "Assessing Range of Motion to Evaluate the Adverse Effects of Ill-Fitting Cervical Orthoses", The Spine Journal, vol. 9, 2009, pp. 225-231.

Karason et al. "Evaluation of Clinical Efficacy and Safety of Cervical Trauma Collars: Differences in Immobilization, Effect on Jugular Venous Pressure and Patient Comfort", Scandinavian Journal of Trauma, Resuscitation and Emergency Medicine, 2014, pp. 1-7.

Product Brochure, "Capital Collar Enhanced", DeRoyal, 2014, 2 Pages.

Product Brochure, "Miami J Advanced by OSSUR", www.ossur.com, 2012, 4 Pages.

Product Brochure, "Miami J Cervical Collar", www.ossur.com, 1 Page.

Product Brochure, "Proglide Cervical Collar", OPTEC, www.optecusa.com, 1 Page.

Product Brochure, "Vista Upper Spine", Aspen Medical Products, 2015, 6 Pages.

Product Brochure, "Instructions for Use Eclipse Cervical Collar", VQ OrthoCare, 2015, 2 Pages.

(56) References Cited

OTHER PUBLICATIONS

Partial International Search Report from PCT Application No. PCT/US2017/050206, Dec. 5, 2017.

* cited by examiner

CERVICAL COLLAR

CROSS-REFERENCE TO RELATED APPLICATIONS

This disclosure incorporates by reference U.S. Pat. No. 5,632,722, granted May 27, 1997, U.S. Pat. No. 6,254,560, granted Jul. 3, 2001, U.S. Pat. No. 7,981,068, granted Jul. 19, 2011, U.S. Pat. No. 8,038,636, granted Oct. 18, 2011, U.S. Pat. No. 8,679,044, granted Mar. 25, 2014, U.S. patent application publication no. 2013/0310722 published on Nov. 21, 2013, and U.S. patent application publication no. 2016/0287424, published Oct. 6, 2016.

This disclosure incorporates by reference U.S. provisional application No. 62/396,279, filed on Sep. 19, 2016, U.S. provisional application No. 62/430,258, filed on Dec. 5, 2016, and U.S. provisional application No. 62/504,121, filed on May 10, 2017.

FIELD OF THE DISCLOSURE

The present disclosure relates to an orthopedic device, and more specifically to cervical collars having height adjustability at a front part, while providing a platform for securing known other components of a cervical collar thereto without significantly modifying their anatomical contours and connection to the height adjusted components.

BACKGROUND

Cervical collars are used for treating conditions of the neck and the cervical spine by cervical spine immobilization. These collars may handle whiplash and other such injuries, where support for the head and neck of the patient is needed, and function to partially immobilize the head and neck of the patient, and to relieve spasm or strain to which the neck muscles of the patient might be subjected by transferring weight or force from the head of the patient to the shoulders or adjacent areas of the patient. Other collars may be arranged for complete or near complete immobilization of the head and neck of the patient to reduce risk of secondary damage to the spinal cord.

A challenge in designing a cervical collar is balancing desired immobilization with user comfort, such as venous pressure. Immobilization may be measured by five planes of movement, including flexion, extension, lateral tilt to right and left, and rotation of the neck to right and left, which are collectively considered generally as cervical range of motion (CROM).

Unfortunately, many patients using cervical collars develop decubitus or decubitus ulcers (also known as bed sores, pressure sores, or trophic ulcers) when wearing cervical collars. These ailments, which involve a breakdown of tissue overlying a bone, arise when tissues overlying a bony prominence are subjected to prolonged pressure against an object such as a cervical collar. Besides impacting superficial tissues such as the skin, decubitus and decubitus ulcers also can aggravate muscle and bone. Restrictive collars are one of the common causes of skin breakdown in the trauma population. As pressure-ulcers are among the most common, yet serious and costly, complications of routine spinal immobilization, it is desirable to provide cervical collars that minimize the probability of ulcers.

Moisture and pressure are two major factors which contribute to the formation of decubitus. Once a decubitus ulcer forms, there is no good method of determining the extent of tissue damage. Further, once started, decubitus can continue to progress through the skin and fat tissue to muscle and eventually to the bone, and is very difficult to treat and arrest. In extreme cases, surgical replacement of bone, muscle, and skin are required to restore that portion of the body of the patient where decubitus has formed.

It is desirable to eliminate or at least minimize the effect of pressure points when using cervical collars. The likelihood of contracting decubitus can be greatly reduced by a more even distribution of pressure to several parts of the body of the patient.

Multiple studies have evaluated CROM and the likelihood of tissue-interface pressure (TIP) exerted by commercially-available cervical collars. One of the known commercial collars that has proven successful at striking the balance of minimal TIP and most restriction of CROM is the Miami J collar (Össur, hf, Reykjavik, Iceland). Multiple studies have validated the features of the Miami J collar, including: Tescher, A. N. et al. *Range-of-motion restriction and craniofacial tissue-interface pressure from four cervical collars*, Journal of Trauma-Injury Infection & Critical Care 63; 5; 1120-1126 (2007); Jacobson, T. M. et al. *Efforts to reduce occipital pressure ulcers*. Journal of Nursing Care Quality, 23; 3; 283-288 (2008); Karason, S. et al., *Evaluation of clinical efficacy and safety of cervical trauma collars, differences in immobilization, effect on jugular pressure and patient comfort*, Scandinavian Journal of Trauma, Resuscitation and Emergency Medicine, 22:37 (2014).

The Miami J collar is also described in U.S. Pat. No. 5,632,722, granted May 27, 1997; U.S. Pat. No. 6,254,560, granted Jul. 3, 2001; U.S. Pat. No. 6,921,376, granted Jul. 26, 2005. Variations of the Miami J collar, embodying the Miami J Advance collar, are described in U.S. Pat. No. 7,981,068, granted Jul. 19, 2011, and U.S. Pat. No. 8,679,044, granted Mar. 25, 2014.

An important feature, preferably included in cervical collars to overcome limited adaptability to accommodate the body of the patient and the particular ailment prompting the need for wearing a cervical collar, is the facility for adjusting the relative positions of various components of the cervical collar. Part of the effectiveness of the Miami J collar is due to its ability for customization to different anatomical sizes of users.

As taught in U.S. Pat. No. 6,254,560, the Miami J collar has supports that enable customized pressure distribution and avoid skin breakdown. A front part of the Miami J collar has an adjustable upper support for the mandibular, chin and/or jaw of the user, and mounted to a lower support or sternum brace by means which permit relative movement between the upper support and the lower support. The posterior component or back part of the Miami J collar has an occipital support mounted to a back support by means which permit relative sliding movement between the occipital support and the back support. The shape of the upper support and occipital support are anatomically optimized for superior immobilization and patient comfort.

FIG. 1 exemplifies a known version of the Miami J collar 100, as taught in the aforementioned patents and publications, particularly U.S. Pat. Nos. 5,632,722 and 6,254,560. The collar 100 generally includes an anterior component 102 and a posterior component 104 connected to one another by a strap system 116. The anterior component 102 has a main support 106 defining a frontal opening 124, and secures to an upper support 108 intended to support the mandibular, jaw, or chin of the user. The upper support 108 is connected to the main support 106 at side sections by a side connection 120, and is connected at a front section by a front connection 122, and lacks height adjustability while the collar 100 is being worn. Padding 112 lines the anterior and posterior components 102, 104.

The anterior component 102 defines a sternal support 110 forming an extension adapted to extend below the clavicle of a user and rest against the sternum. The sternal support 110 carries a sternum pad 114 to avoid decubitus over long periods of wear of the collar 100. The sternum pad 114 typically has a fixed thickness, and lacks adjustability in the sense that when worn it applies constant pressure.

The posterior component 104 comprises lower and upper parts 126, 128, with the upper part 128 serving as an occipital support. The lower and upper parts 126, 128 are connected to one another by a posterior connection 124. Although not shown, the posterior component 104 may be unitary and monolithic comprising a single part in contrast to the two parts depicted in FIG. 1, and resemble the posterior component taught by U.S. Pat. No. 7,981,068 and found in the Miami J Advance collar.

The upper support 128 and the anterior and posterior components 102, 104 are generally symmetrical about a vertical center line, and may be formed from rigid or semi-rigid plastic. The material forming the upper support 128 and the anterior and posterior components 102, 104 may be flexible prior to donning the collar 100, but sufficiently rigid once the collar 100 is donned to resist yielding due to weight exerted by the user.

Both the upper support 128 and the occipital support of the Miami J collar 100 are uniquely anatomically shaped to maximize comfort and immobilization while minimizing pressure on the user. Because the upper support 128 and the occipital support of the Miami J collar 100 are clinically proven, it is desired that any improvements over the current Miami J collar 100 provide means for preserving the function and shape of the upper support 128 and occipital support of the current Miami J collar 100.

Another challenge in designing a cervical collar is providing convenient yet reliable height adjustment of sternum support elements. Sternum support elements normally connect to an anterior portion of a cervical collar via struts or connections that define an anterior aperture that allows clinicians, physicians, and first responders to gain access to a user's trachea for medical procedures and examinations without removal of the collar. Because the sternum support normally attaches to both left and right sides of the anterior portion of the collar in order to define this aperture, adjusting the height of the sternum support requires the inconvenient and potentially uneven adjustment of both left- and right-sided complementary adjustment apparatuses.

Another challenge is the design of the adjustment apparatuses themselves. There is a problem of adjustment apparatuses being clumsy and inconvenient for a clinician to operate quickly and easily, and especially for a user to operate while wearing the device on their own neck.

Moreover, height adjustment apparatuses are sometimes unfortunately designed in such a way that a user or clinician may inadvertently touch the apparatus in a way that tampers with or adjusts the height in an unplanned and/or undesired way. A desired feature of a cervical collar is therefore a height adjustment apparatus that, while convenient to operate, is not susceptible to accidental adjustments or tampering.

Yet another challenge is the ability of a clinician or user to easily adjust the flexibility of pressure exerted by the sternum support of a cervical collar. At certain times, such as during every day, long-term use, a user may need to have greater flexibility for flexion of the neck, i.e. moving the chin toward the sternum. At other times, such as during first response procedures or medical procedures, a user may need to be immobilized from flexion of the neck by exerting greater pressure on the sternum. There is a problem of cervical collars not offering a convenient yet effective method for switching between the collar allowing flexion and disallowing flexion.

Another challenge is that existing cervical collars often comprise inadequate or inconvenient strap systems. For example, straps may attach via hook and loop fastener to inconvenient locations on the body of the cervical collar, leading to difficulty in donning the collar correctly and/or consistently. Straps may not be configured to attach closely to the body of the cervical collar and consequently jut out therefrom, leading potentially to damage, injury, inconvenience, and/or unintended removal of or tampering with the collar if the straps catch on an object or are unintentionally pulled, adjusted, or released by a user, clinician, or others.

Existing cervical collars often comprise inadequate or poorly-fitted posterior components. For example, posterior components may be overly simplistic in design, comprising flat profiles and no features to mitigate pressure points along the occiput. These designs can lead to or exacerbate decubitus and discomfort.

In light of the foregoing considerations, there is a further need for a cervical collar with a height adjustment mechanism on the sternum support that provides for a convenient, effective method for allowing or restricting flexion and is easily and accurately adjustable in height without allowing accidental tampering with the height, as well as an improved strap system for connecting anterior and posterior components of a cervical collar, and an improved shape for a posterior component of a cervical collar.

SUMMARY

The present disclosure describes an improved cervical collar for restricting head and neck movement to promote healing after an injury to the spinal column. The cervical collar has height, circumferential and angular adjustment to accommodate a wide variety of patient sizes and anatomical configurations, and to accommodate dimensional changes caused by increased or decreased swelling of the affected anatomical portions of the patients during treatment of the injury. The cervical collar is arranged to stabilize and immobilize the cervical area, by restricting lateral, sagittal, and coronal movement, while improving comfort and fit for individual patients.

Embodiments of the disclosure relate to a cervical collar having a height adjustment system between supports forming an anterior component, which permit the use of known supports in the cervical collar to maintain their functionality, comfort, and fit, including their anatomical contours and connection to the height adjusted components. Embodiments of the disclosure also relate to an improved strap system for cervical collars. Yet further embodiments of the disclosure relate to improved posterior components for cervical collars.

The height adjustment system is arranged for adjusting the chin height in a simple and effective manner that limits or mitigates tampering with the height while the collar is worn. The height adjustment system preferably includes using incremental height adjustment so the height may be locked at a desired height setting. The height adjustment system may be arranged to allow usage in existing collar designs, such as the Miami J or Miami J Advance collars, without substantially altering the shape and function of the upper support and posterior component including an occipital support.

The height adjustment system mitigates or eliminates the need for pre-sizing methods, and is provided in a simplified manner to enable many height settings customizable for different users. The height adjustment system allows for the use of known upper and posterior components, which have been on the market for many years to serve many users of cervical collars, and are clinically proven for their efficacy.

The height adjustment system allows for improved placement and configuration of a cervical collar on patients of different heights, which makes adjustment possible and easy while the collar is being worn. The upper support and posterior component can be properly fitted against the chin and head of a patient by a clinician, followed by the extension of the anterior component against the patient's chest. Likewise, the anterior component may be placed against the patient's chest and the upper support and posterior component can then be extended to the chin and head of the patient. The height setting can then be locked at the desired height setting by the clinician to ensure a proper fit for the user.

To avoid inadvertent adjustment of the collar height during use, locking means are provided in combination with the height adjustment system. While the height adjustment system arrests the height of the collar, the locking means offers another level of locking in addition to the height adjustment system.

Unlike in the prior art where the lower support and corresponding sternum pad are fixed, embodiments of the disclosure permit selective adjustment of pressure applied to the sternum of the user, particularly by locking or unlocking flexibility of the lower support.

Embodiments described herein provide a strap system that improves circumferential pressure exerted about the neck of the user by offering greater extension of the strap about the user's neck, and thus the cervical collar. The strap system is arranged to facilitate donning and doffing of the cervical collar by offering improved means for attaching and detaching the anterior component from the posterior component. The anterior and posterior components offer greater circumferential adjustability to accommodate different user anatomical sizes, healing phases, padding thickness, and other reasons for adjusting collar circumference. The strap system further reduces damage, injury, or inadvertent adjustment of the collar due to its improved system for maintaining strap ends close to or flush against the body of the strap.

The posterior component in the embodiments offers improved pressure relief properties for areas of a user about the posterior component, and about a user's spinal column. The posterior component is contoured to adapt to the strap while maintaining its pressure relieving properties. Indeed, the posterior component is arranged to provide improved anterior-posterior and lateral occipital support by way of its improved shape, attachment features, and other features on both the inner and outer side of the posterior component.

These and other features, aspects, and advantages of the present disclosure will become better understood regarding the following description, appended claims, and accompanying drawings.

Figure 1:
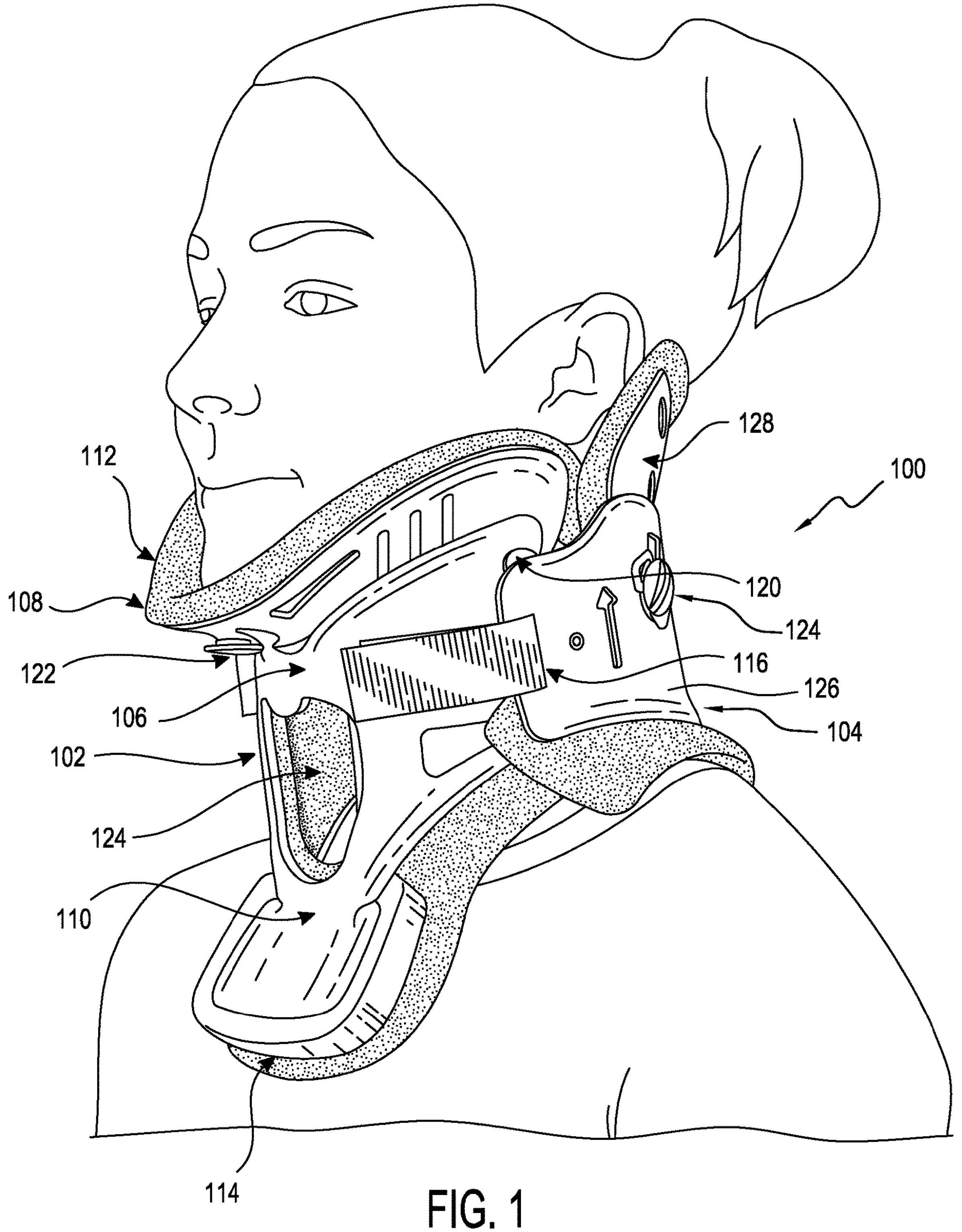
FIG. 1 (Prior Art)
FIG. 1 is a perspective view of a prior art cervical collar.

The drawing figures are not necessarily drawn to scale, but instead are drawn to provide a better understanding of the components thereof, and are not intended to be limiting in scope, but to provide exemplary illustrations. The figures illustrate exemplary configurations of a cervical collar, and in no way limit the structures or configurations of a cervical collar according to the present disclosure.

DETAILED DESCRIPTION OF VARIOUS EMBODIMENTS

A. Introduction

Embodiments of an orthopedic device are provided for stabilizing and supporting anatomical portions of a user, for example, the neck and head of a user.

Although the embodiments of the disclosure are adapted for supporting and stabilizing anatomical portions of many users having various anatomical shapes and sizes, the embodiments of the disclosure may also be dimensioned to accommodate different types, shapes and sizes of anatomical portions.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

While the foregoing embodiments have been described and shown, alternatives and modifications of these embodiments, such as those suggested by others may be made to fall within the scope of the invention. While the cervical collar has been described in combination with collar parts, it will be understood that the principles described may be extended to other types of orthopedic and prosthetic devices.

Reference characters are provided in the claims for explanatory purposes only and are not intended to limit the scope of the claims or restrict each claim limitation to the element in the drawings and identified by the reference character.

For ease of understanding the disclosed embodiments of a cervical collar, the front or anterior, and rear or posterior portions of the cervical collar are described independently. The anterior and posterior portions of the cervical collar function together to form a supporting and stabilizing cervical collar that encompasses the anatomical portions of the user.

The term "posterior" also has its ordinary meaning and refers to a location that is behind or to the rear of another location. The term "anterior" has its ordinary meaning and refers to a location ahead of or to the front of another location.

The terms "rigid," "flexible," "compliant," and "resilient" may be used herein to distinguish characteristics of portions of certain features of the cervical collar. The term "rigid" is intended to denote that an element of the collar is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. As for the term "semi-rigid," this term is used to connote properties of support members or shells that provide support and are free-standing, however such support members or shells may have some degree of flexibility or resiliency.

The term "flexible" should denote that features are capable of repeated bending such that the features may be bent into retained shapes or the features do not retain a general shape, but continuously deform when force is applied. The term "compressible" may be used to qualify such structural features as being capable of being reduced in size or volume due to the exertion of force applied to the structural feature.

B. Embodiments of the Cervical Collar

Figure 2:
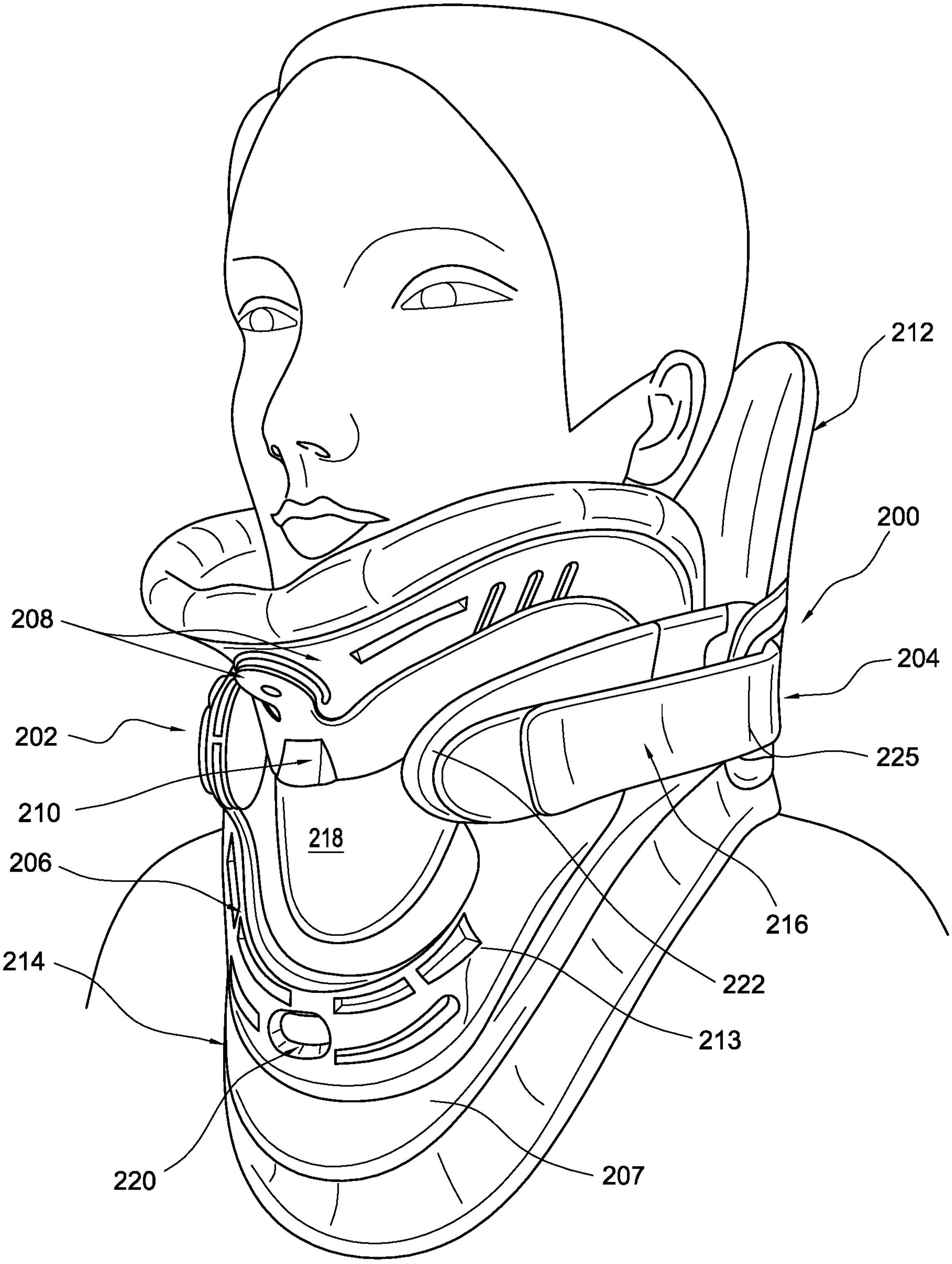
FIG. 2 is a perspective view of an embodiment of a cervical collar according to the present disclosure.
Figure 3:
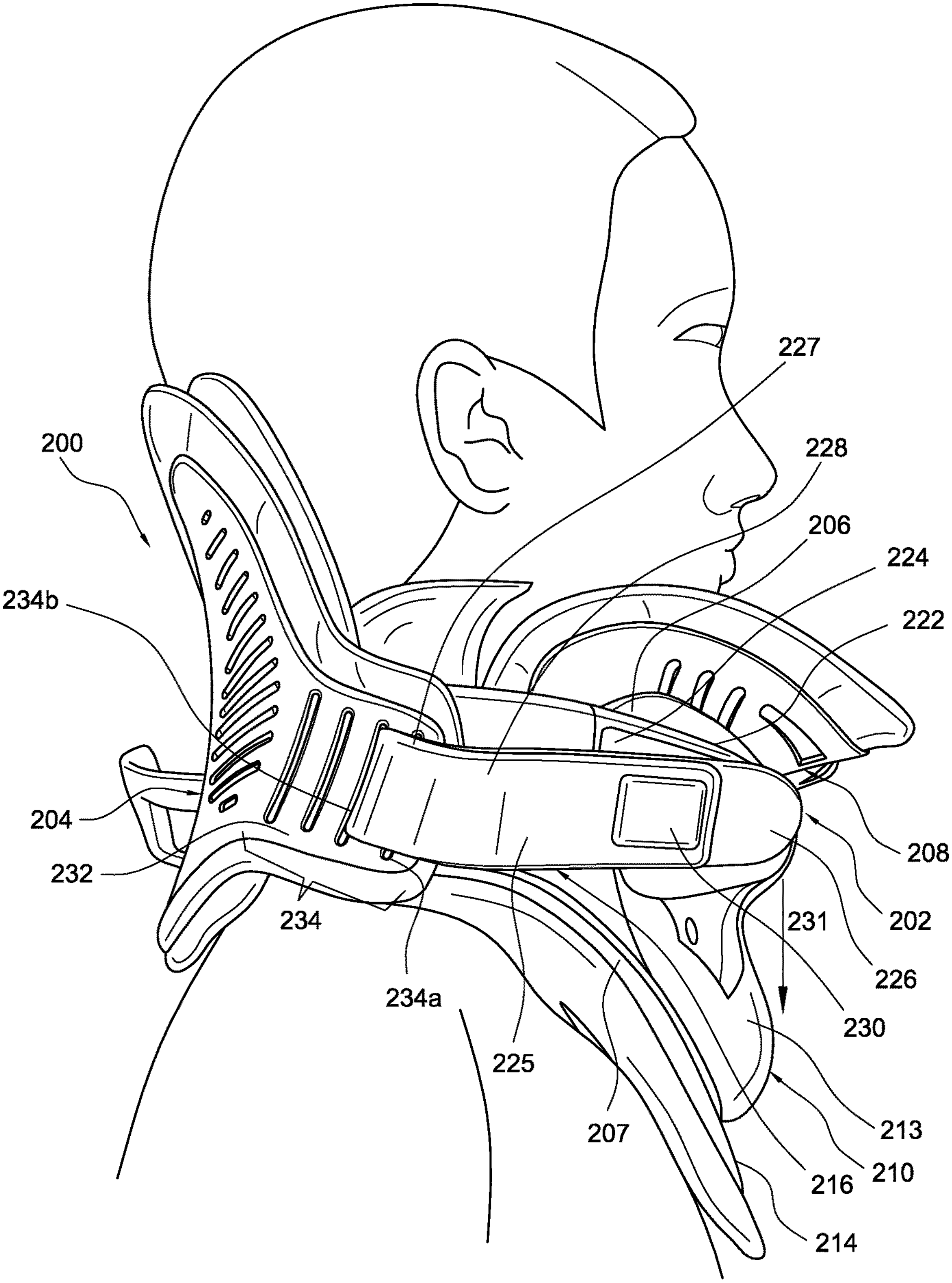
FIG. 3 is a side elevational view of the cervical collar embodiment of FIG. 2.

FIGS. 2 and 3 exemplify an embodiment of a cervical collar 200 of the disclosure. The cervical collar 200 includes an anterior component 202 that secures to a posterior component 204 by a strap system 216. The anterior component 202 includes a main support 206 upon which the strap system 216 is preferably secured, and has a sternum section 214 that extends to the sternum of a user. The sternum section 214 is formed at least in part by a base component 207 upon which a cover 213 (which may alternatively be called a front casing) housing at least part of an adjustment mechanism 220 is disposed.

An intermediate support 210 secures to the main support 206, and is adjustable relative to the main support 206 by an adjustment mechanism 220. The intermediate support 210 and the main support 206 together form a frontal opening 218. An upper support 208 (which may alternatively be called a chin tray) is located on the intermediate support 210 above the main support 206. Padding 212 is located along the anterior and posterior components 202, 204.

Referring specifically to FIG. 3, the strap system 216 is shown in one of several preferred configurations. Specifically, the strap system 216 includes straps 225 located on opposed sides of the collar 200, and extending between the anterior and posterior components 202, 204. Each strap 225 is elongate and has first and second segments 226, 228. The first segment 226 is mounted onto a frontal projection 222 of the main support 206.

Frontal projections 222 extend toward and over a top portion of the frontal opening 218. The frontal projections 222 preferably extend anteriorly past and over the adjustment mechanism 220, as will be evident in following embodiments of the adjustment mechanism 220. Likewise, the frontal projections 222 enclose at least part of the intermediate support 210, by extending over a front surface of the intermediate support 210, and provide greater support to the intermediate support 210 about the user. The frontal projections 222, at least in exterior or outwardly portions thereof, are preferably rigid or semi rigid along a circumferential or arcuate profile of the intermediate support 210 to provide support to the upper and intermediate supports 208, 210. In this manner, the frontal projections 222 do not yield or bend when the strap system 216 is secured thereon in combination with the posterior component 204 about a neck of a user.

By extending forwardly, the frontal projections 222 provide a portion on the surface of the anterior component 202 for receiving and corresponding to straps 225. Straps 225 may thus be advantageously adjacent to and/or flush against the anterior component 202 as opposed to jutting outwardly from the collar 200. This is in contrast to existing collars where straps freely jut outwardly from the collar, leading to risk of inadvertent adjustment, damage to the collar, or injury to a user if the straps are inadvertently tampered with.

The frontal projections 222 enable a stable platform upon which the strap system 216 can secure and preferably does not interfere with the upper support 208, thereby allowing removal of the strap system 216, or on one side thereof without adjusting the integrity of the intermediate support 210, and the upper support 208. The additional length provided by the frontal projections 222, by which they extend over the frontal opening 218, offers greater adjustability for the strap system 216, thereby offering more accommodation to users' neck circumferences.

The frontal projections 222 serve to stabilize the force exerted by the user's chin by generally extending over the main support 206, as evidenced by force 231, which generally coincides downwardly with a lower portion of the main support 206. As the frontal projections 222 straddle the intermediate support 210, the main support 206 is arranged obliquely downwardly relative to the frontal projections 222, which generally jut horizontally and preferably parallel to a user's mandible.

As will be explained below, the intermediate support 210, while carrying the upper support 208, moves relative to the main support 206 and does not interfere with the strap system 216 during height adjustment of the anterior component 202 of the collar 200. In this manner, the strap system 216 remains intact while securing the anterior and posterior components 202, 204 to one another. The anterior component 202 can be advantageously adjusted for height while the collar 200 is being worn by the user since the intermediate support 210 (and hence upper support 208) is moved relative to the main support 206, but the relationship between main support 206 and posterior component 204 is uninterrupted and unchanged.

The arrangement of the strap system 216 in combination with the frontal projections 222 enables a clinician to don and size the collar 200 on the user in either direction (i.e. either toward the chin or toward the sternum). Specifically, the clinician may place the upper support 208 against a user's chin, and then use the adjustment mechanism 220 to drop the main support 206 via the intermediate support 210 to the appropriate size to abut the user's sternum. The strap system 216 may first be appropriately secured to the anterior and posterior components 202, 204, or secured after the collar 200 has been appropriately sized. Alternatively, the main support 206 may be placed against a user's sternum, and secured to the posterior component 204 by the strap system 216. The clinician may then use the adjustment mechanism 220 to selectively adjust the upper support 208 via the intermediate support 210 to the appropriate height so as to abut the user's chin, while the collar 200 is already secured to the user.

The posterior component 204 defines side extensions 232 that define a series of strap slots 234 for securing the straps 225 to the frontal projections 222. In the depicted embodiment, the straps 225 each have a first segment 226 secured to a fastener 224 on the frontal projections 222. The first strap segment 226 may be configured in shape to correspond to a shape of the corresponding frontal projection 222. The strap 225 is looped at loop segment 227 about at least one of the strap slots of the series of strap slots 234. In this embodiment, the strap 225 loops through first and second slots 234*a*, 234*b* of the series of straps slots 234. The series of strap slots 234 may define at least two of such strap slots, and in the depicted embodiment the series of strap slots 234 include four strap slots. The clinician may select which strap slots of the series of strap slots 234 to loop the strap 225 according to the size of the user.

A second strap segment 228 extends from the looped segment 227 and secures over a surface of the first strap segment 226 via a fastener 230, thereby pulling the posterior component 204 toward the anterior component 202 at the loop segment 227. In this manner, when the strap 225 is looped about the series of strap slots 234, the anterior and posterior components 202, 204 are already secured to one another, and further tensioning and tightening of the strap 225 can be achieved without the necessity of holding the posterior component 204 relative to the anterior component 202.

The straps 225 can be tensioned on both sides of the collar 200 simultaneously, or adjusted individually according to the demands of the user. This strap system 216 allows for removal of the collar 200 by only requiring removal of one of the straps 225 on one of the sides of the collar 200 from the corresponding fastener 230. Because the first segment 226 of the strap 225 remains in place, the user does not need to significantly resize the strap system 216 upon repeated steps of donning and doffing of the collar 200, particularly when only one of the straps 225 has its second segment 228 detached from the surface of the first segment 226 for removing the collar 200, while leaving the other strap 225 intact and secured. By minimizing the inconvenience of resizing the strap system 216 upon donning and doffing, user compliance is enhanced especially over long-term use.

The side extensions 232 preferably extend over the main support 206 so as not to interfere with the anterior component 202, which generally bears a significant amount of weight of the user's head and neck and in order to facilitate treatment of a user's injury. As noted above, while the side extensions 232 extend over the main support 206, they do not interfere with the height adjustment of the anterior component 202 since the side extensions 232 extend over the main support 206 and below the upper and intermediate supports 208, 210.

Figure 4:
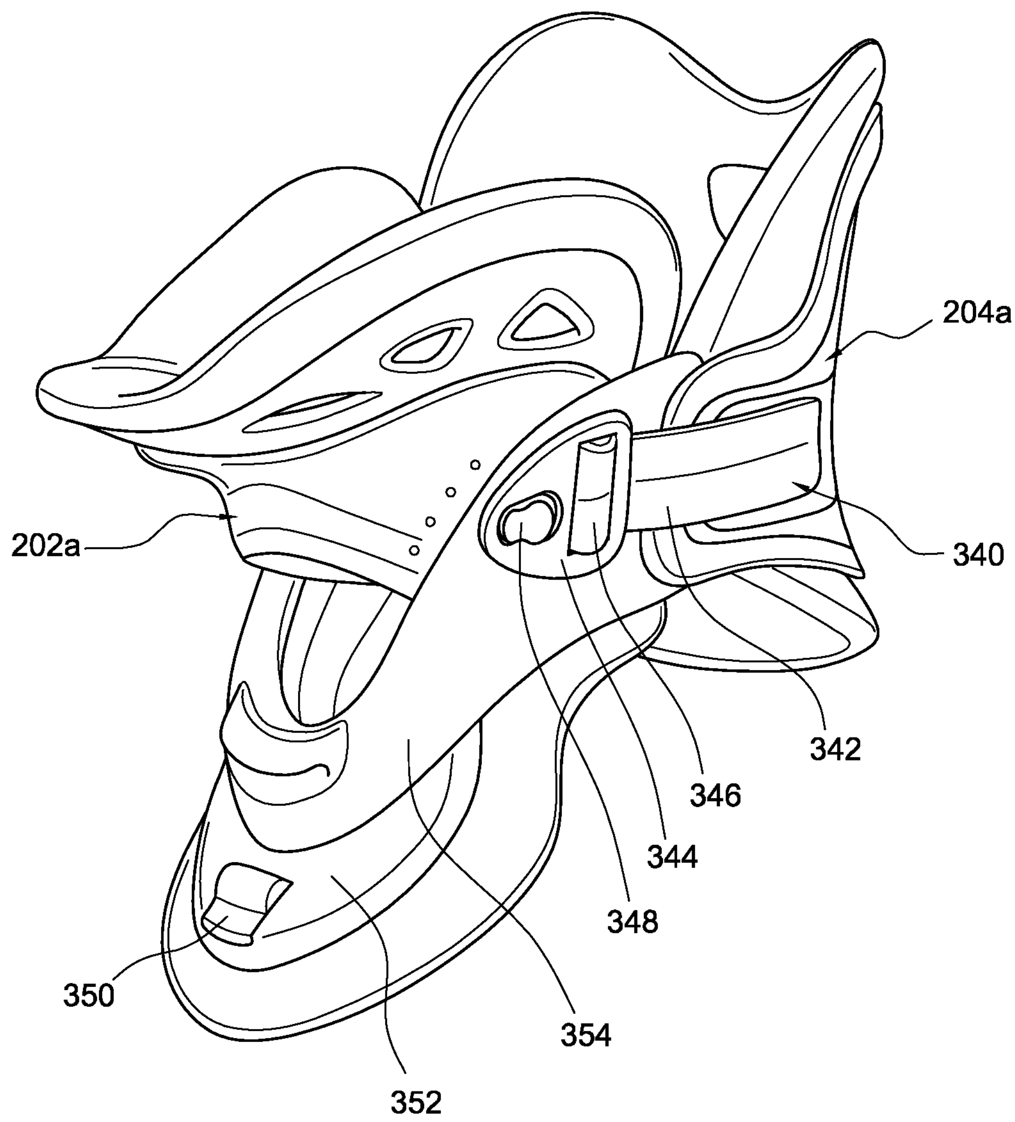
FIG. 4 is a perspective view of another embodiment of the cervical collar of FIG. 2.

FIG. 4 exemplifies another embodiment of a strap system 340. In this embodiment, a strap 342 extends from the posterior component 204*a* and carries a mounting part 344. The mounting part 344 may be a buckle, latch, ring, or other suitable part that can be carried by the strap 342 and engage an anchor 348 located on the anterior component 202*a*. The anchor 348 may comprise a hook protruding from a side of the anterior component 202*a*. The strap 342 is looped and secured about the mounting part 344 for length adjustment at loop 346, and may likewise be looped about the posterior component 204*a* in the preceding embodiment, or attached to the posterior component 204*a* whereby length adjustment is made relative to the mounting part 344.

In this embodiment, the strap 344 can quickly be attached and detached from the anterior component 202*a*. Such an arrangement may be preferable to a user in that the strap length may be set by the clinician, and does not require subsequent adjustment by the user. This convenient arrangement of strap 344 allows a user to easily don and doff the collar repeatedly with minimal or no re-sizing required, thus enhancing compliance and comfort for a user, especially for long-term use.

FIG. 4 also exemplifies how a main support 354 is separate from a sternum support 352. The sternum and main supports 352, 354 may be selectively adjusted relative to one another by a sternum adjustment mechanism 350.

Figure 5A:
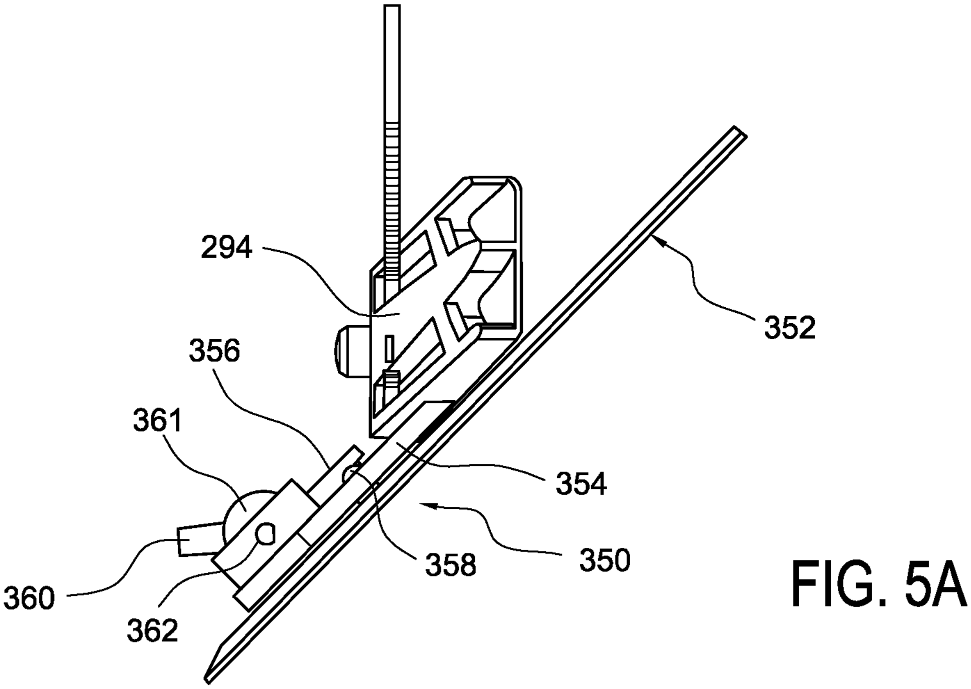
FIG. 5A is a schematic view of a sternal height mechanism in a lowered configuration.
Figure 5B:
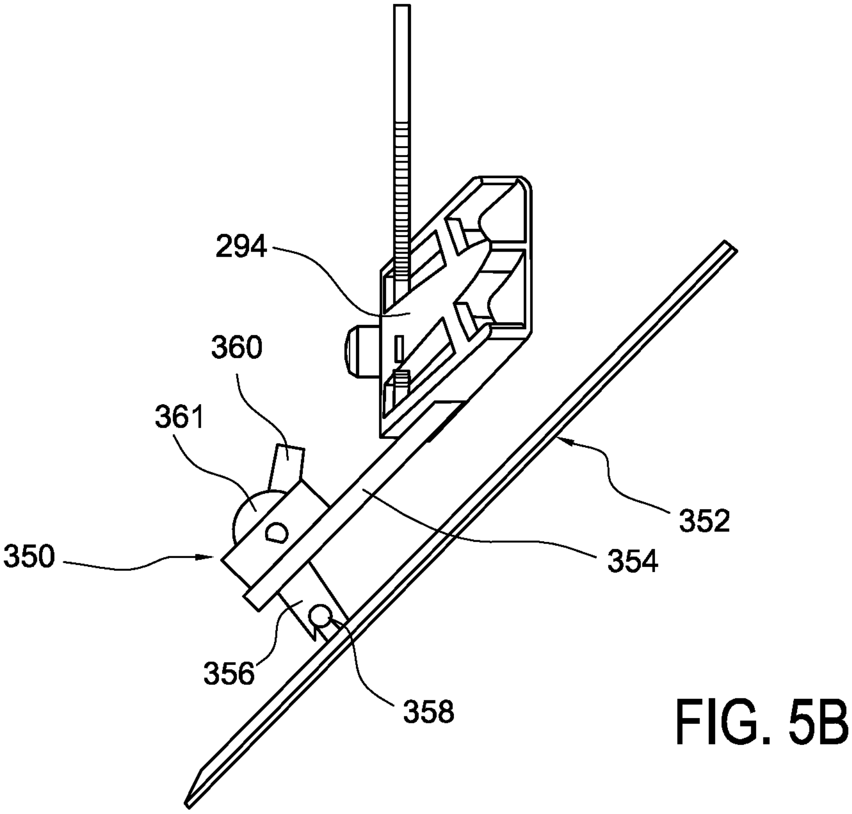
FIG. 5B is a schematic view of the sternal height mechanism of FIG. 5A in a raised configuration.

FIGS. 5A and 5B illustrate an exemplary embodiment of the sternum adjustment mechanism 350, wherein the sternum support 352 is adjustable relative to the main support 354, to provide differing pressure against the sternum of the user or to provide pressure release. The main support 354 may carry the sternum adjustment mechanism 350 which pivotally connects to the sternum support 352 by a linkage 356 and anchor 358. The sternum adjustment mechanism 350 includes a lever 360 on a cam 361. The cam 361 is rotatable relative to a biasing element 362, and articulates the linkage 356 upon rotation of the cam 361.

FIG. 5A shows the sternum adjustment mechanism 350 in a lowered or collapsed configuration such that the lever 360 is pulled forward to collapse the linkage 356, and the sternum support 352 generally abuts the main support 354. In this manner, there is pressure relief against the sternum. FIG. 5B shows the sternum adjustment mechanism 350 in a raised or extended configuration such that the lever 360 is articulated rearward, and the cam 361 engages the biasing element 362 to maintain the linkage 356 in the extended configuration. The sternum support 352 is extended away from the main support 354 by the linkage 356.

Figure 6A:
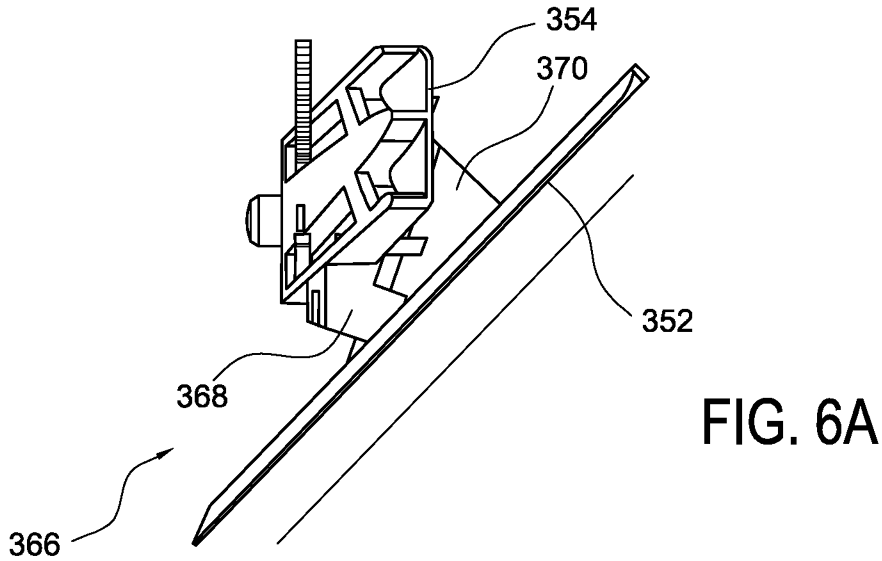
FIG. 6A is a schematic view of a variation of the sternal height mechanism in FIG. 5A in a lowered configuration.
Figure 6B:
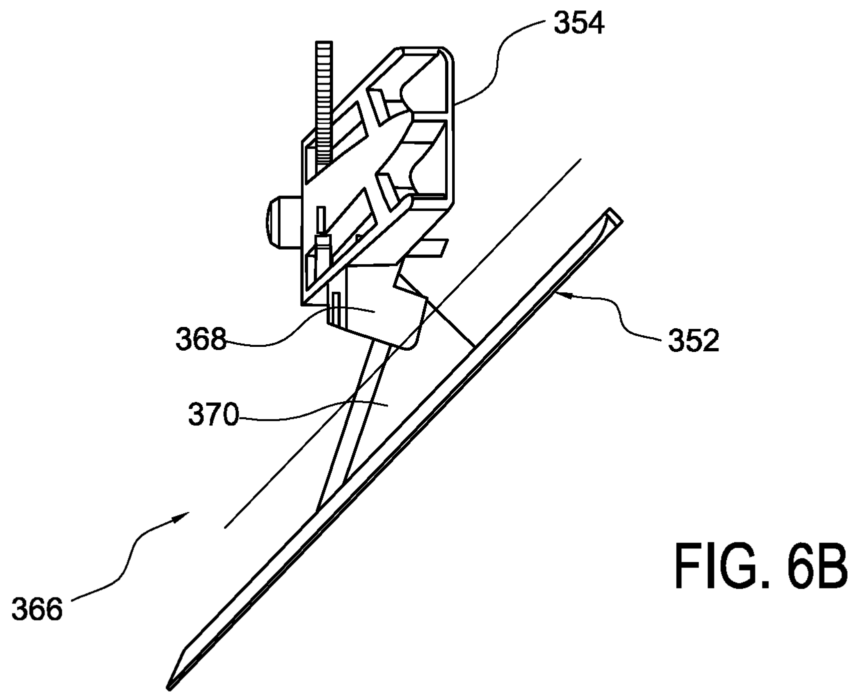
FIG. 6B is a schematic view of the sternal height mechanism of FIG. 6A in a raised configuration.

FIGS. 6A and 6B illustrate another exemplary embodiment of a sternum adjustment mechanism 366. In this embodiment, the sternum adjustment mechanism 366 comprises a ramp 370 extending from the sternum support 352. The main support 354 carries a bracket 368 that is slidable along the ramp 370. The bracket 368 may include a cam surface or other suitable mechanism, such that as the bracket 368 slides along the ramp 370 in a raised or extended configuration in FIG. 6B, the bracket 368 can be retained along the ramp 370 at a fixed position to extend the sternum support 352 relative to the main support 354 according to a height of the ramp 370. In the lowered or collapsed configuration of FIG. 6A, the bracket 368 is located at a different position along the ramp 370 to bring the sternum support 352 adjacent or near the main support 354.

Figure 7:
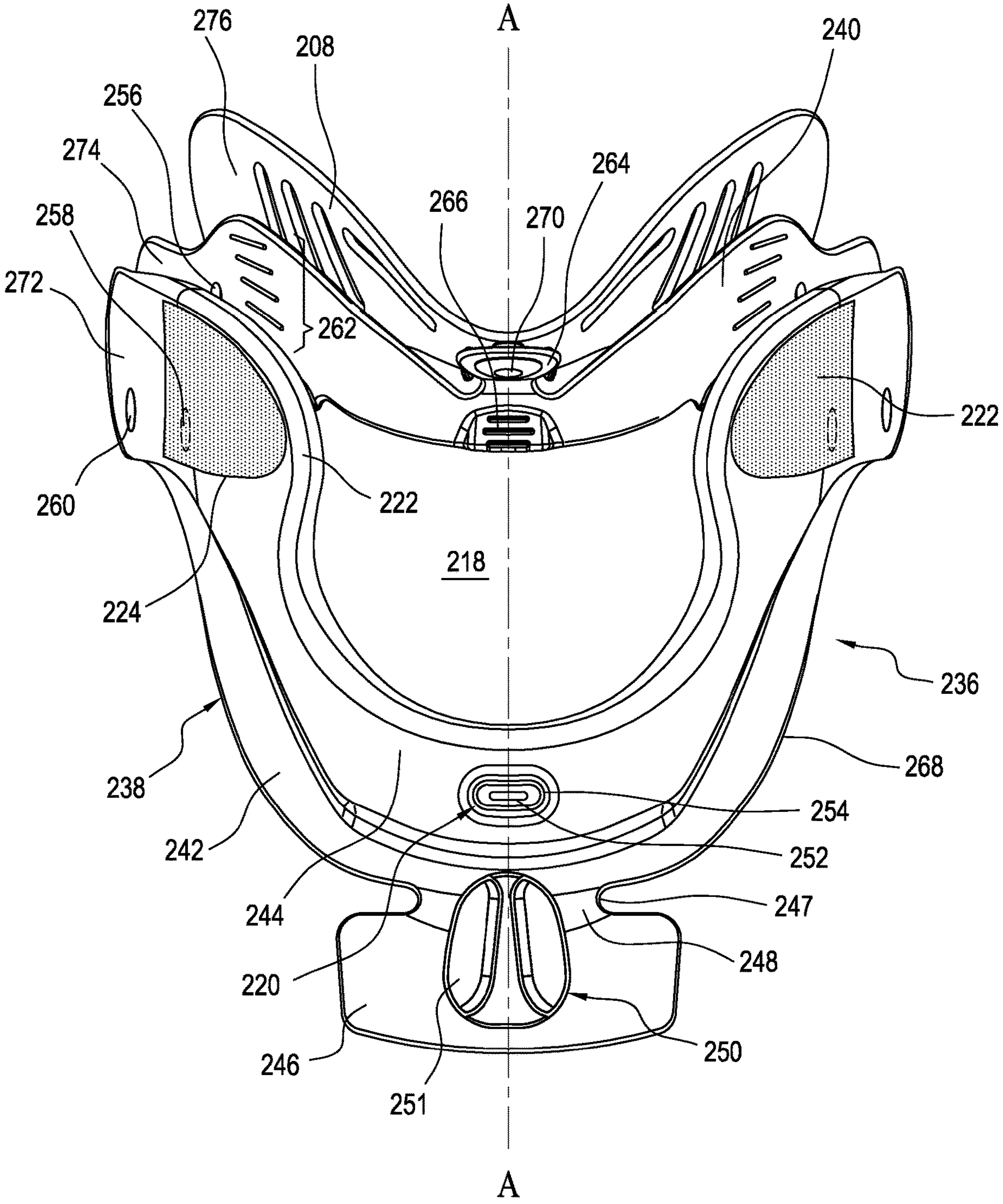
FIG. 7 is a front elevational view of a variation of the anterior component in the cervical collar of FIG. 2.
Figure 8:
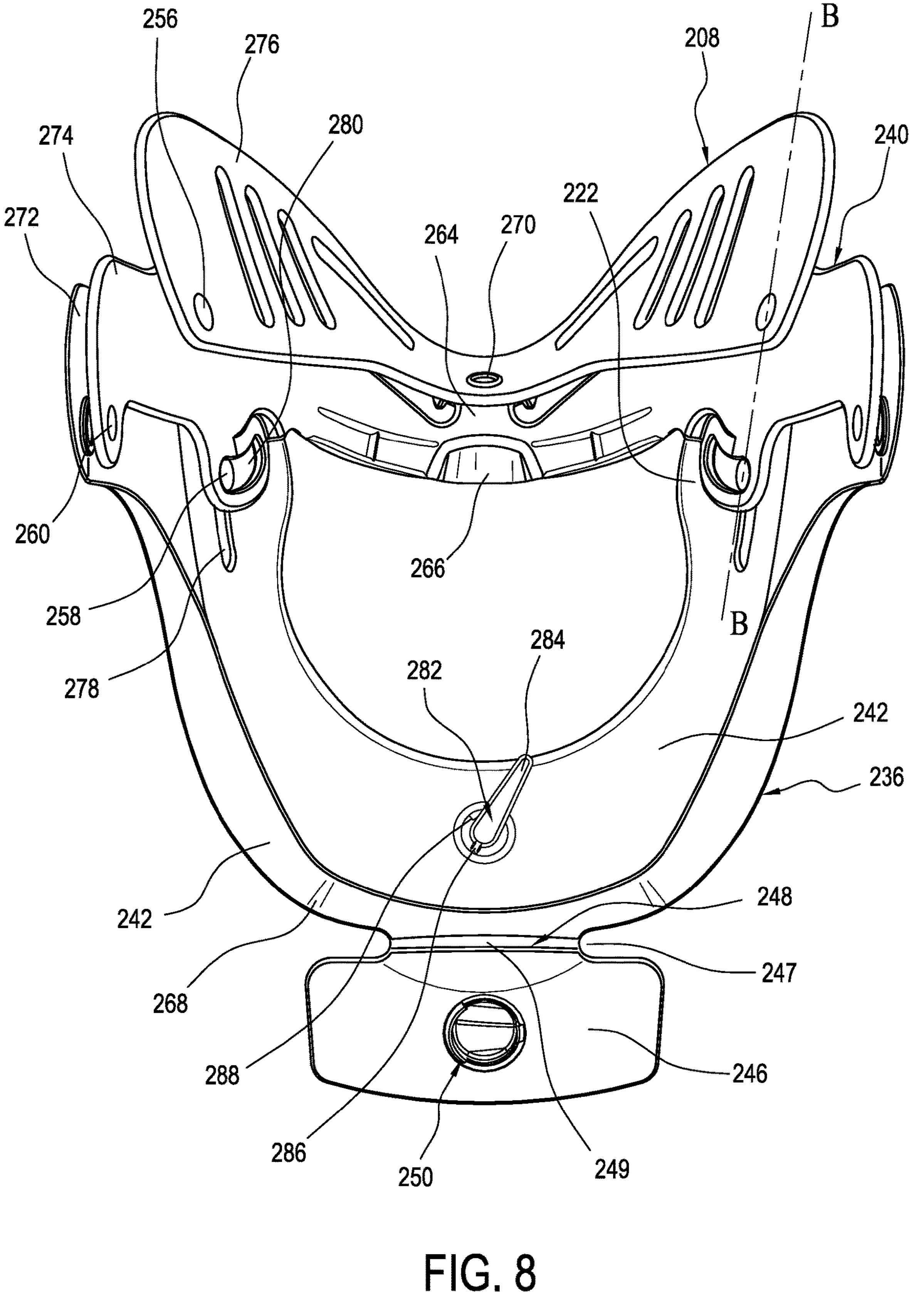
FIG. 8 is a rear elevational view of the anterior component of FIG. 7.

FIGS. 7 and 8 depict an alternative embodiment of an anterior component 236 over the anterior component of FIGS. 2 and 3. The anterior component 236 has both a main support 238 and intermediate support 240, and the intermediate support 240 is adapted to receive the upper support 208 of the embodiment of FIGS. 2 and 3, and the Miami J collar.

The upper support 208 is suspended on the intermediate support 240 by being connected at a central tab 264 of the intermediate support 240 extending outwardly relative to an upper periphery of the intermediate support 240 and secured by a pin 270 along a central axis A-A along the front of the anterior component 236. A grip 266 may be provided below the central tab 264, and extend along the periphery of the frontal opening 218 and a lower periphery of the intermediate support 240. The grip 266 may have tactile features to aid grasping the grip 266, and the grip 266 may protrude outwardly from the periphery of the intermediate support 240 to offer a relief portion for placing a finger or thumb for raising the intermediate support 240 relative to the main support 238.

The upper support 208 has flanks 276 that connect and run on the inside of the intermediate support 240. The flanks 276 have end portions at which side connections 256 secure to the intermediate support 240. Thus the upper support 208 is suspended centrally by the central tab 264 and the side connections 256, thereby enabling to the upper support 208 to contour to the anatomy of the chin and mandibles of the user, and offer improved comfort. The intermediate support 240 may define a scale 262 above the frontal projections 222 so as to provide a relative sizing of the collar 200.

The intermediate support 240 connects to the main support 238 by sliding connections 258 for accommodating height adjustment of the anterior component 236. The sliding connections 258 are arranged to couple slots 280, preferably having a curved shape, defined by the intermediate support 240, and slots 278, preferably having a curved shape, defined by the main support 238. The sliding connections 258 may be located and vertically stacked below the side connections 256 to stabilize the upper support 208, so as to align generally along a stacking axis B-B regardless of the height setting. The intermediate support 240 has flanks 274 that connect to flanks 272 of the main support 238 at pivot points 260, which accommodate sliding movement of the side connections 256 along the slots 278, 280.

The main support 238 includes a base 242 adapted to be placed adjacent to the user, and a cover 244 adapted to house and cover the adjustment mechanism 220. The base 242 and cover 244 form the side extensions 222, whereby the fastener 224 may be placed over the cover 244. A sternum section 246 extends from the base 242 at a transition 247 between the base 242 and the sternum section 246. The transition 247 may comprise a narrowed or thinned section from the base 242 and extending to the sternum section 246. The sternum section 246 may be formed continuously with the base 242 so the sternum section 246 is unitary with the base 242, or alternatively is attached to the base 242.

The base 242 may define side grips 268 on opposed sides of the sternum support 246. The side grips 268 may be defined by raised portions of the base 242 that enable a clinician to grip and hold the base 242 when adjusting the height of the anterior component 236.

According to the depicted embodiment, the sternum section 246 is connected to the base 242 by a hinge 248 at the transition 247. The hinge 248 may be formed as a living hinge formed from a recessed channel 249 on a rear side of the base 244. Alternatively, the hinge 248 may comprise a compliant portion of the base 242 that bends upon application of force.

Figure 9A:
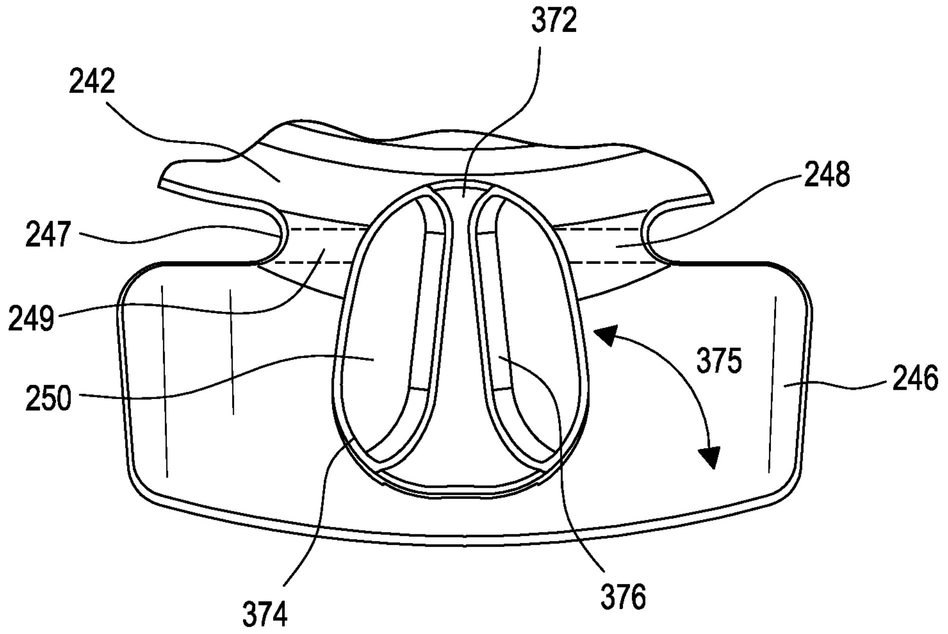
FIG. 9A is a schematic view of a sternal relief device in the cervical collar of FIG. 2 in a stiff configuration.
Figure 9B:
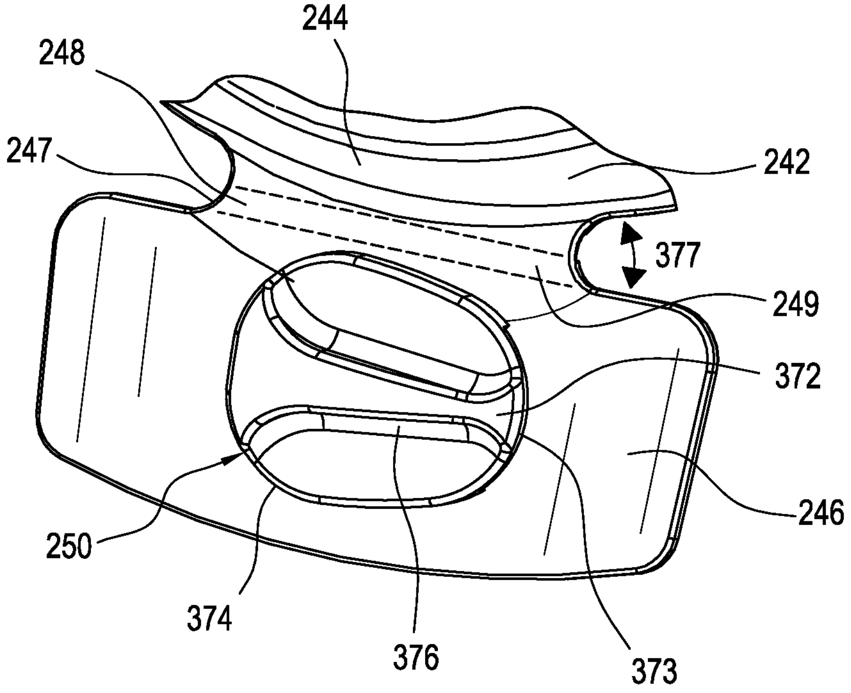
FIG. 9B is a schematic view of the sternal relief device of FIG. 9B in a relief configuration.

As illustrated in more detail in FIGS. 9A and 9B, a stiffener mechanism 250 may be carried by the sternum section 246 to stiffen the hinge 248 of the sternum section 246 relative to the base 242. The ability to modify the stiffness of the sternum section 246 is advantageous to provide pressure relief to the user, particularly when sternal or thoracic support is unnecessary or when the user requires minor adjustment of the neck. The stiffener mechanism 250 includes a first portion 372 arranged to selectively extend over the transition 247 and the hinge 248 to prevent or substantially prevent bending of the sternum section 246 away from the base 242. The first portion 372 preferably extends past the hinge 248, as shown in FIG. 9A, to assure the first portion 372 blocks movement of the hinge 248.

The first portion 372 may extend proximate to the cover 244, however is sized so as not to interfere with the cover 244 upon rotation of the stiffener mechanism 250. The first portion 372 may have a recessed tip 373 so as not to interfere with the cover 244 upon rotation.

The stiffener mechanism 250 has a second portion 374 extending from the first portion 372, and pivotally mounted on the sternum section 246. In the preferred embodiment, the second portion 374 is limited in rotation 375 relative to the sternum section 246 so as to assure a stiffened position and a released position of the stiffener mechanism 250. For example, the rotation 375 of the second portion 374 may only be 90 degrees.

The second portion 374 may include a tactile feature 376 to facilitate grasping of the stiffener mechanism 250 from a stiffened position thereby preventing flexure of the sternum section 246 away from the user's sternum, as depicted in FIG. 9A. The first portion 372 blocks movement of the hinge 248. FIG. 9B depicts a released position whereby the sternum section 246 has a flexure 377 both toward and away from a user's sternum, such that the first portion 372 is clear from the hinge 248.

In a variation, when the hinge 248 is formed by a recessed channel 249, the recessed channel 249 may have a sufficient depth to facilitate cutting the sternum section 246 from the base 242. Alternatively, the transition 247 may be formed to make trimming thereof easy so that a clinician may be able to remove the sternum section 246 along a peripheral contour of the base 242.

As shown in FIG. 7, the adjustment mechanism 220 is located generally along the central axis A-A at the cover 244 and above the sternum section 246. The adjustment mechanism 220 defines an actuator 252 for actuating the adjustment mechanism 220, and permitting adjustment in height of the intermediate support 240 relative to the main support 238. The cover 244 defines a recess 254 about the actuator 252 to facilitate actuation of the actuator 252, and the actuator 252 is located recessed in the recess 254 so as to prevent inadvertent actuation of the actuator 252. The actuator 252 is biased in an engaged position such that when not pressed, the actuator 252 maintains the adjustment mechanism 220 in the engaged position. Upon pressing the actuator 252 toward the rear side of the anterior component 236 and deeper into the recess 254, the adjustment mechanism 220 is placed in a disengaged position to permit adjustment of the height of the anterior component 236.

As shown in FIG. 8, a lock mechanism 282 is provided as extra assurance of locking the adjustment mechanism 220. The lock mechanism 282 is located on the rear side of the anterior component 236. The lock mechanism 282 includes a lever 284 that moves a tab 286 along a limiter 288 for placement between locked and unlocked positions. The limiter 288 may include blocks on opposed sides of an arc of motion relative to the lever 284, for example between 45 degrees. The clinician or user may place fingers over the cover 244 to switch the lever 284 between the locked and unlocked position. In the locked position, the lock mechanism 282 prevents the actuator 252 from being pressed into the disengaged position. In other words, the locked position of the lock mechanism 282 prevents actuation of the actuator 252. In the unlocked position, the actuator 252 may be pressed to disengage the adjustment mechanism 220, and permit height adjustment of the anterior component 236. The lock mechanism 282 offers an extra layer of protection to assure the adjustment mechanism 220 cannot be tampered with or inadvertently adjusted during normal use.

Figure 10A:
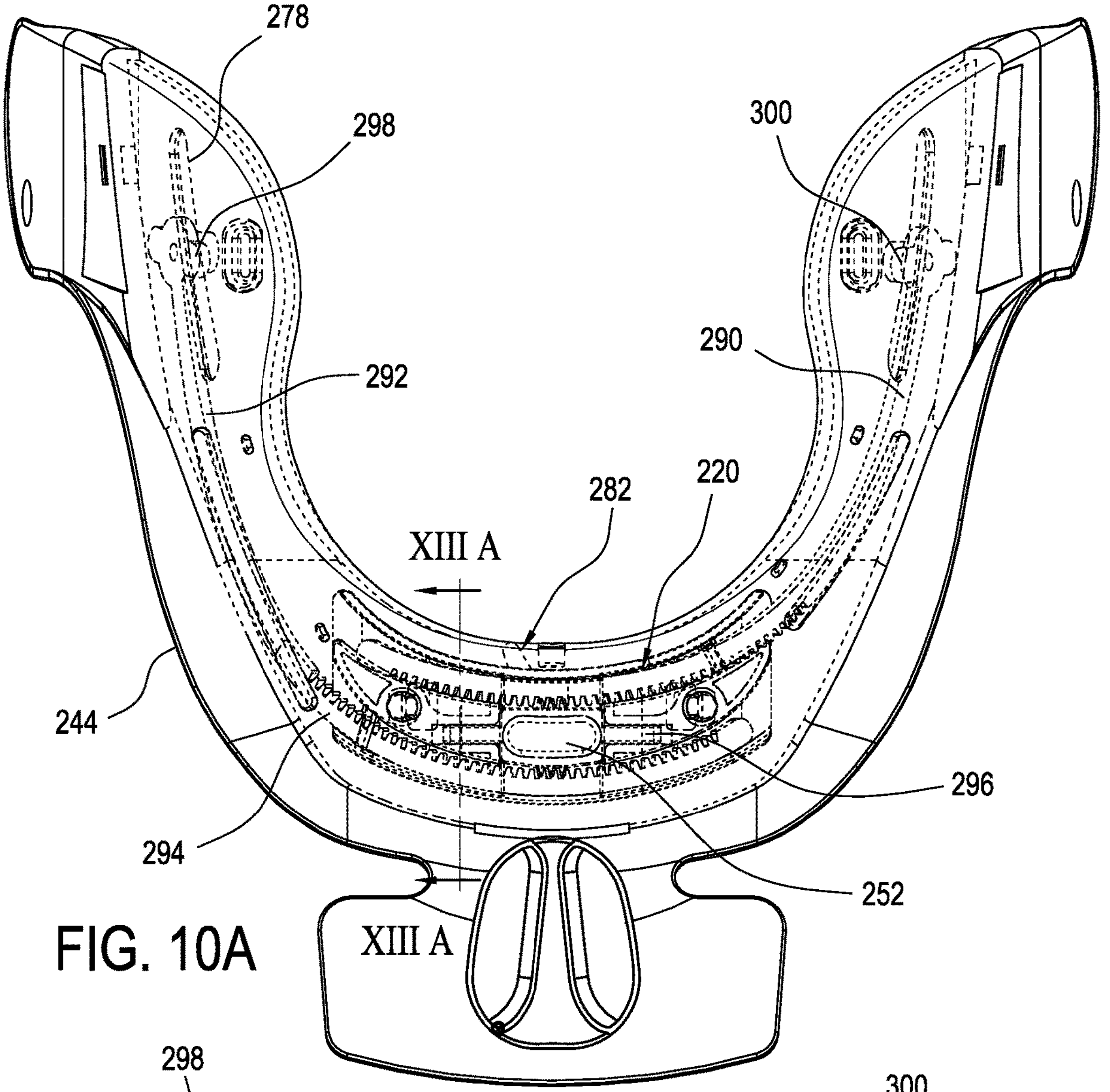
FIG. 10A is a front elevational view of the lower support in the anterior component of FIG. 7 with the lower support depicted in transparent form.
Figure 10B:
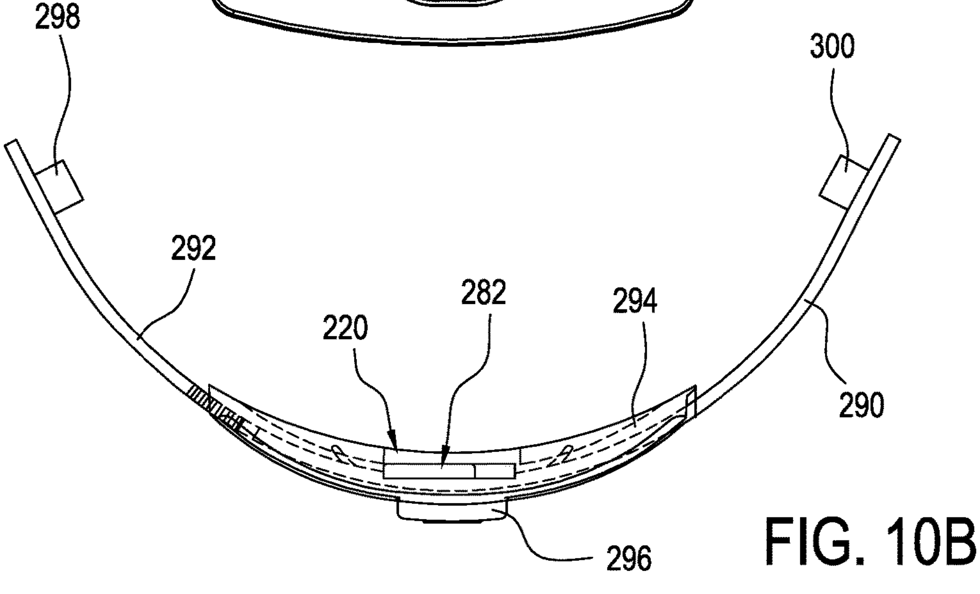
FIG. 10B is a plan view of the adjustment mechanism in FIG. 10A with the lower support removed.

In observing FIGS. 10A and 10B, the adjustment mechanism 220 is shown relative to the cover 244. The adjustment mechanism 220 includes first and second traction elements 290, 292 that slide along a connector 294 at a lower portion of the cover 244, and have end portions extending to the slots 278 of the cover 244. The end portions define bosses 298, 300 adapted to slide along the slots 278. A lock element 296 is connected to and biased against the connector 294. The lock element 296 may form the actuator 252, and is movable relative to the connector 294, to engage and disengage from the first and second traction elements 290, 292.

Figure 11:
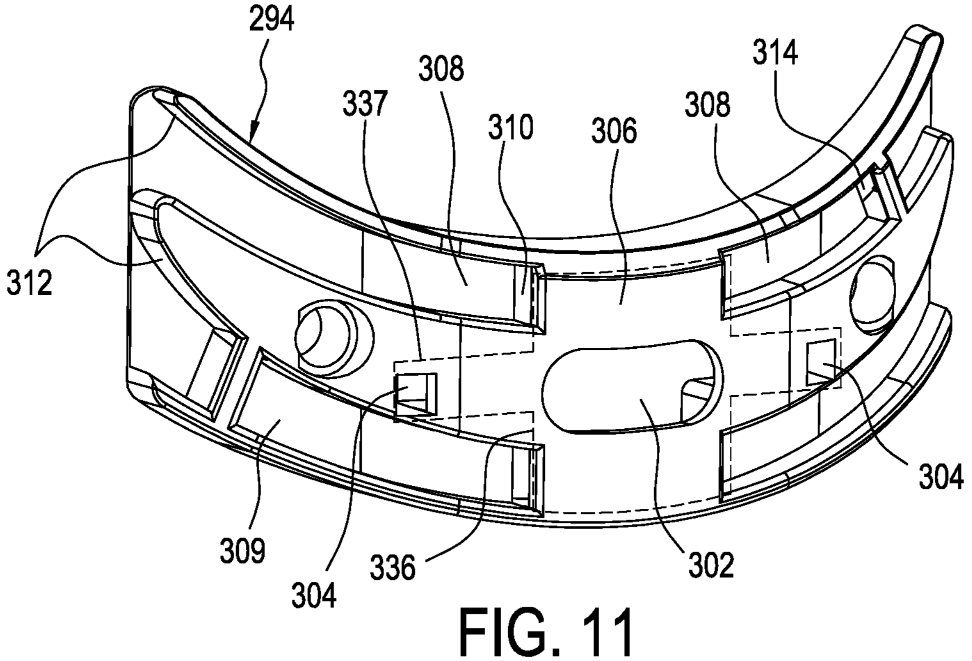
FIG. 11 is a perspective view of the base in the adjustment mechanism of FIG. 10A.

FIG. 11 shows the connector 294 in greater detail. The connector 294 defines an opening 302 for receiving the actuator 252 and openings 304 for receiving end portions 326, 328 (shown in FIG. 12B) of the lock element 296. The connector 294 has a center portion 306 that defines a cavity 336 on a rear side of the connector 294 for receiving a center section 324 of the lock element 296 adjacent the actuator 252, and corresponding curved channels 308, 309 for receiving arms 320, 322 of the lock element 296. The connector 294 forms the curved channels 308, 309 for guiding and receiving the first and second traction elements 290, 292, and peripheral surfaces 312 to the curved channels 308, 309 to direct the first and second traction elements 290, 292 upwardly toward the slots 278. The connector 294 forms center slots 310 through which the first and second traction elements 290, 292 extend to engage the lock element 296, as well as side slots 314 to yet further guide the first and second traction elements 290, 292. To facilitate assembly and manufacture, the connector 294 may be monolithic and defined by a single part.

Figure 12A:
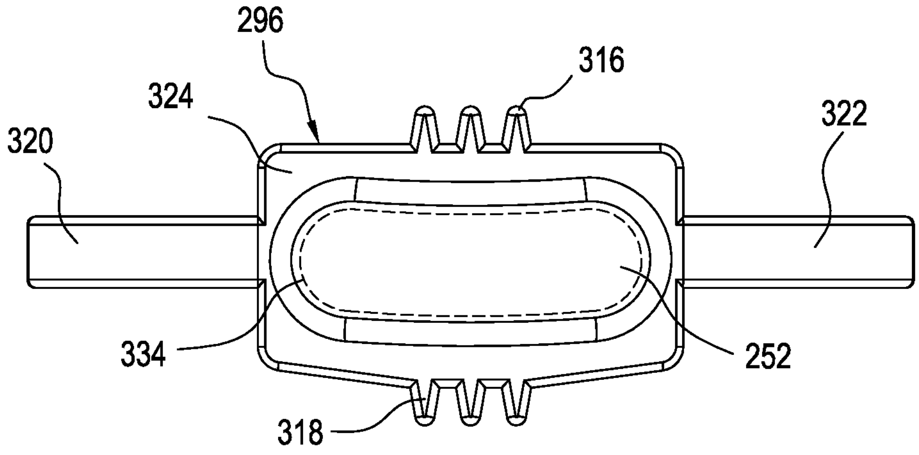
FIG. 12A is an elevational view of the actuator in the adjustment mechanism of FIG. 10A.
Figure 12B:
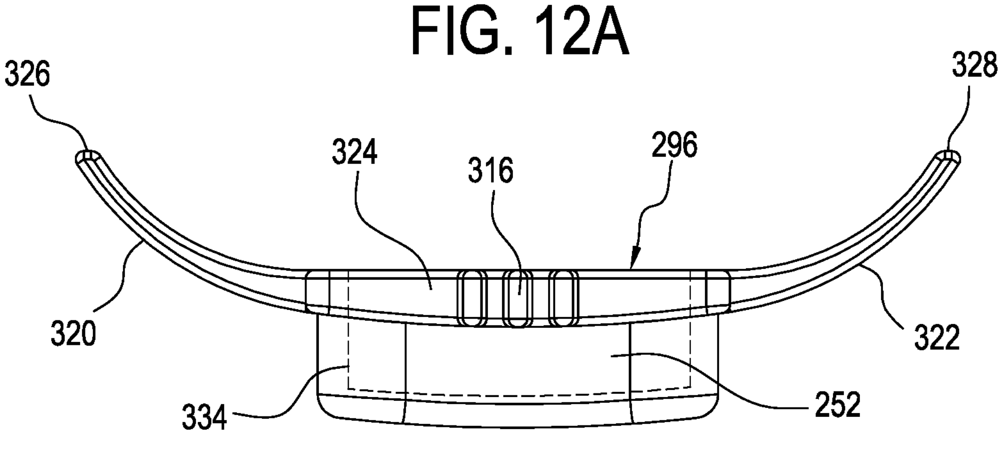
FIG. 12B is a plan view of the actuator in the adjustment mechanism of FIG. 10A.

FIGS. 12A and 12B depict the lock element 296 as having the actuator 252 that protrudes from the center section 324. The center section 324 defines at least one or a series of teeth 316, 318 along upper and lower portions of the lock element 296 for engaging corresponding teeth of the first and second traction elements 290, 292. First and second arms 320, 322 extend curvingly from the center section 324 and bear the end portions 326, 328 that are received by the connector 294. The arms 320, 322 form springs to bias the lock element 296 against the connector 294, particularly in that the end portions 326, 328 engage the connector 294 and the actuator 252 and the teeth 316, 318 can move relative to the opening 302 to actuate the adjustment mechanism 220. To facilitate assembly and manufacture, the lock element 296 may be monolithic and defined by a single part. A rear side of the lock element 296 defines a rear recess 334 for engagement with the at least one post 338 of the lock mechanism 282.

Figure 13A:
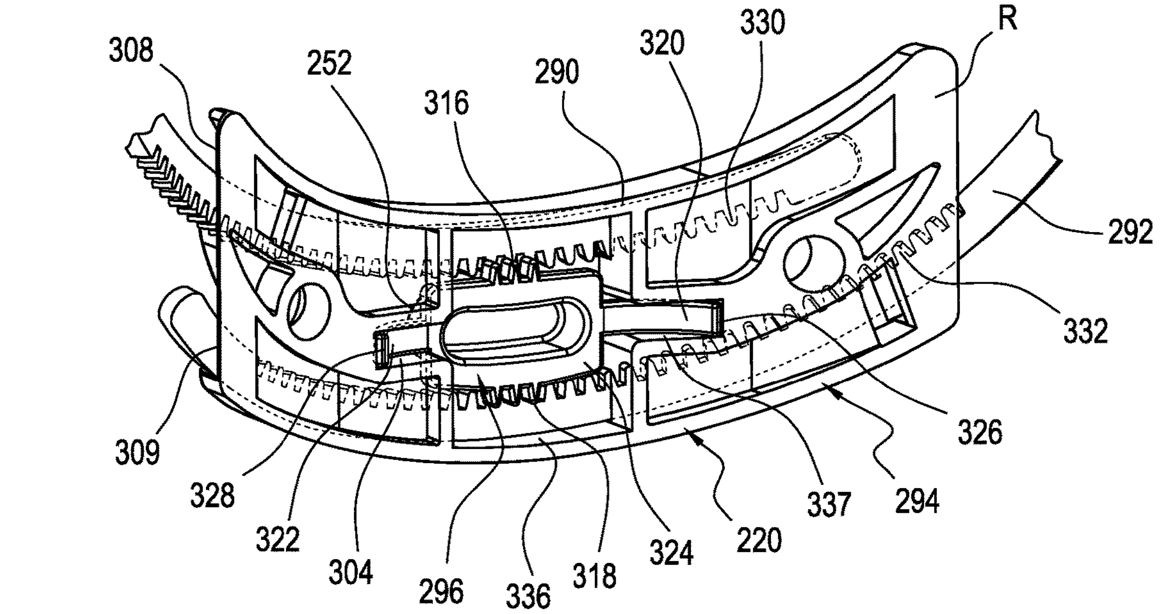
FIG. 13A is a perspective schematic view of the adjustment mechanism of FIG. 10A in an unlocked configuration.
Figure 13B:
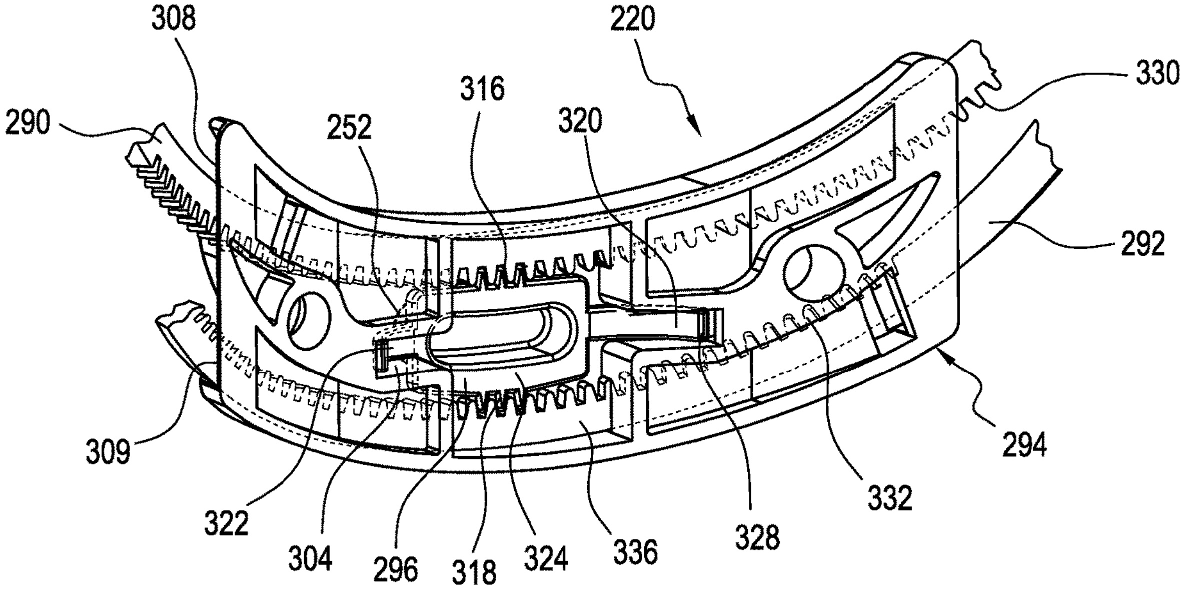
FIG. 13B is a perspective schematic view of the adjustment mechanism of FIG. 10A in a locked configuration.

FIGS. 13A and 13B show how the adjustment mechanism 220 operates to adjust the first and second traction elements 290, 292. Unlike in known cervical collars having a rotatable element forming a rack and pinion adjustment mechanism (which disadvantageously cannot be locked), the adjustment mechanism 220 is arranged to be disengaged upon pressing of the actuator 252, and to automatically lock upon release of the actuator 252. Such an arrangement is advantageous in that the clinician can assure the adjustment mechanism 220 is not inadvertently bumped or adjusted and thereby unintentionally change the height of the collar. Indeed, by pressing the actuator 252 toward the user, as opposed to pulling away, there is greater stability to maintaining the cervical collar 200 on the user without the tendency of adjusting the location of the main support 206.

Upon disengagement of the adjustment mechanism 220, the clinician can modify the location of the upper and intermediate supports 208, 210 relative to the main support 206 with a single hand, as adjustment of the intermediate support 210 can be done freely as the first and second traction elements 290, 292 slide and permit the intermediate support 210 to articulate relative to the main support 206. Such an arrangement provides quicker and stable means for changing the height, and enables the first and second traction elements 290, 292 to include more teeth 330, 332 and thereby more height settings.

As shown in FIG. 13A in the disengaged position, the lock element 296 moves toward and is biased against a rear side R of the connector 294. The first and second end portions 326, 328 are received by the openings 304 of the connector 294, so that they are fixed relative to the connector 294. In the disengaged position, the actuator 252 is pressed or biased against the spring force generated by resistance and flexure of the first and second arms 320, 322. The first and second sets of teeth 316, 318 are drawn toward the rear side of the collar 200 and fully disengage from the teeth 330, 332 of the first and second traction elements 290, 292. The center section 324 and the arms 320, 322 move within the cavity 336 and arm slots 337, such that the center section is 324 drawn away or at least partially away from a biasing surface delimiting part of the cavity 336. The biasing surface of the cavity 336 is located on the rear side of the connector 294. The base 242 may limit the travel of the lock element 296 at the rear side of the connector 294.

As shown in FIG. 13B, upon release of the actuator 252 when the adjustment mechanism 220 is in the engaged position, the lock element 296 is biased against the rear side R of the connector 294 yet extends toward the front side F as a result of first and second arms 320, 322, and the center section 324 being retained and biased against the biasing surface of the cavity 336. The first and second sets of teeth 316, 318 engage the first and second teeth 330, 332 of the first and second traction elements 290, 292. The teeth 316, 318 are preferably arranged in an elongate row to assure there is at least one tooth engaging corresponding teeth of the first and second traction elements 290, 292. The connector 294 is preferably configured so the channels 308, 309 flatten or substantially flatten the first and second traction elements 290, 292 within the center slot 310 so there is multiple engagement of the teeth 316, 318 with the corresponding teeth 330, 332 of the first and second traction elements 290, 292. The adjustment mechanism 220 is arranged so the natural or predetermined position is the engaged position so that when the actuator 252 is released, the teeth 316, 318 of the lock element 296 and the first and second traction elements 290, 292 engage one another.

The adjustment mechanism 220 is not limited to using the connector 294 and lock element 296 described above, but rather it may include means for providing engagement and disengagement from teeth or other locking elements on the first and second traction elements 290, 292, preferably but not limited to automatic engagement upon release of the adjustment mechanism 220. The adjustment mechanism 220 is arranged for engaging the first and second traction elements 290, 292 in an engaged position, and is further arranged to disengage from the first and second traction elements 290, 292 in a disengaged position. In the disengaged position, a clinician can selectively adjust the height of the intermediate support 210, and hence the upper support 208, relative to the main support 206 with restriction of gradual adjustment, but can accomplish the feat of height adjustment of the anterior component 236 quickly upon disengagement of the adjustment mechanism 220 and automatic locking at the desired location upon release of the adjustment mechanism 220 so it engages the first and second traction elements 290, 292 in a fixed location.

Figure 14A:
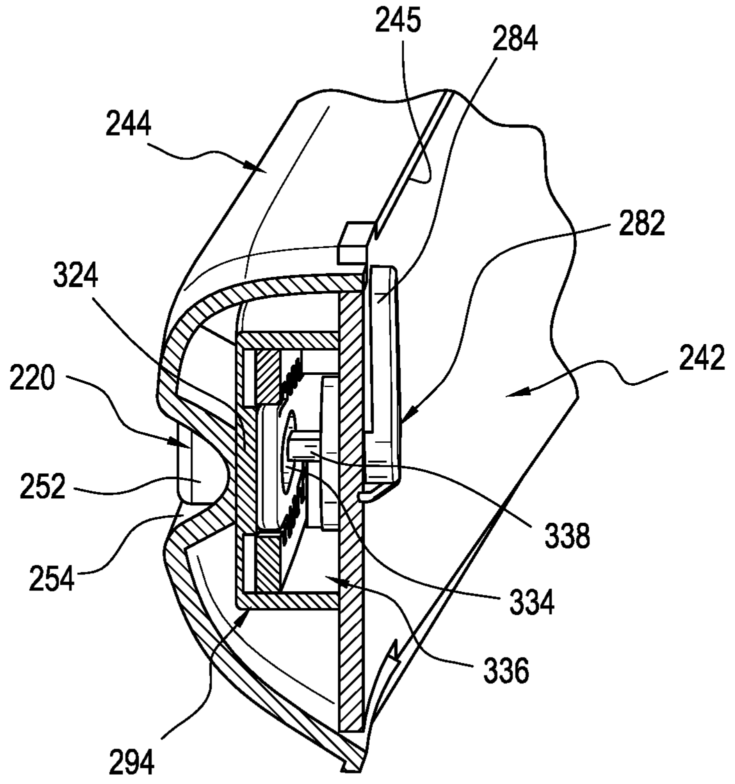
FIG. 14A is a perspective schematic view taken along line XIVA-XIVA in FIG. 10A of the lock mechanism in the locked configuration.
Figure 14B:
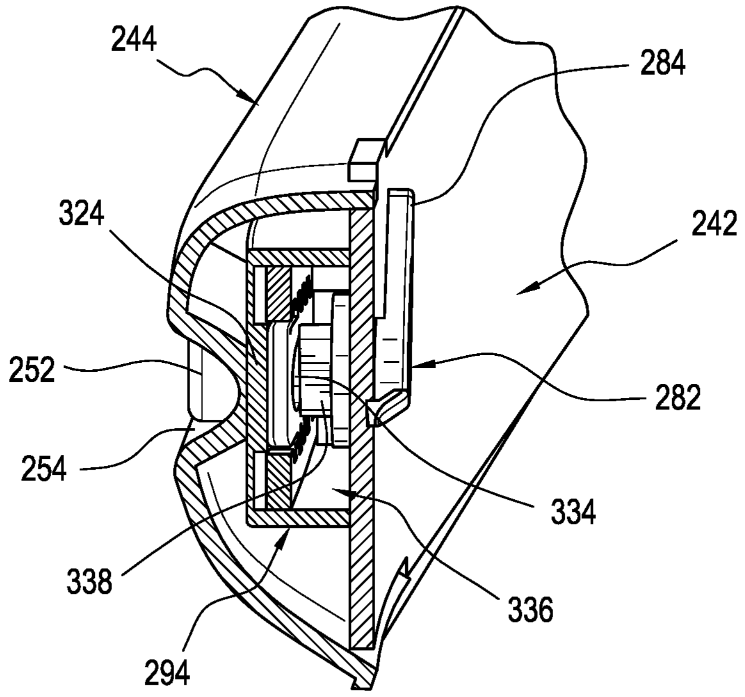
FIG. 14B is a perspective schematic view of the lock mechanism in FIG. 10A in the unlocked configuration.

FIGS. 14A and 14B exemplify the lock mechanism 282 that may be used in combination with the adjustment mechanism 220. The lock mechanism 282 includes a lever 284 that may extend above or just below the inner periphery 245 of the base 242 in order to facilitate adjustment of the lock mechanism 282 without requiring removal of the cervical collar 200. The lever 284 may include at least one post 338 extending inwardly and on an opposite side of the base 242 as the lever 284. The at least one post 338 is directed toward the rear cavity 336 opposite the actuator 252.

The at least one post 338 is adapted to rotate according to the position of the lever 284. In an unlocked position, the at least one post 338 is located within the rear recess 334, and the actuator 252 can be pressed without interference by the at least one post 338 since the rear recess 334 takes up the at least one post 338 when the actuator 252 is pressed toward the rear of the anterior component 236 or the base 242. In the lock position, the lever 284 is rotated so that the at least one post 338 interferes with the center section 324 of the lock element 296 since the at least one post 338 is out of alignment with the rear recess 334.

Figure 15A:
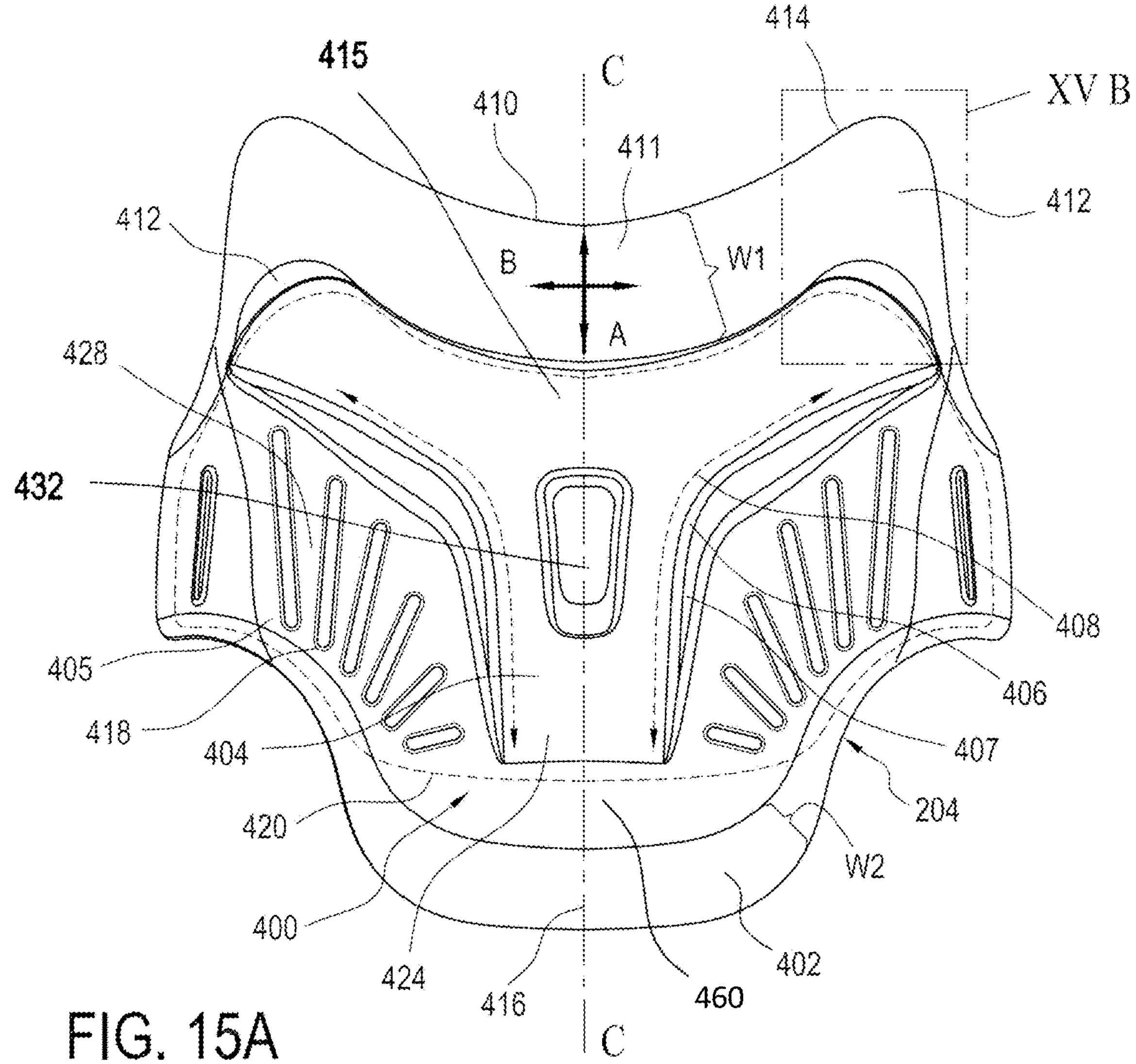
FIG. 15A is an elevational view of a variation of the posterior component in the cervical collar of FIG. 2 showing an outer side of the posterior component.
Figure 15B:
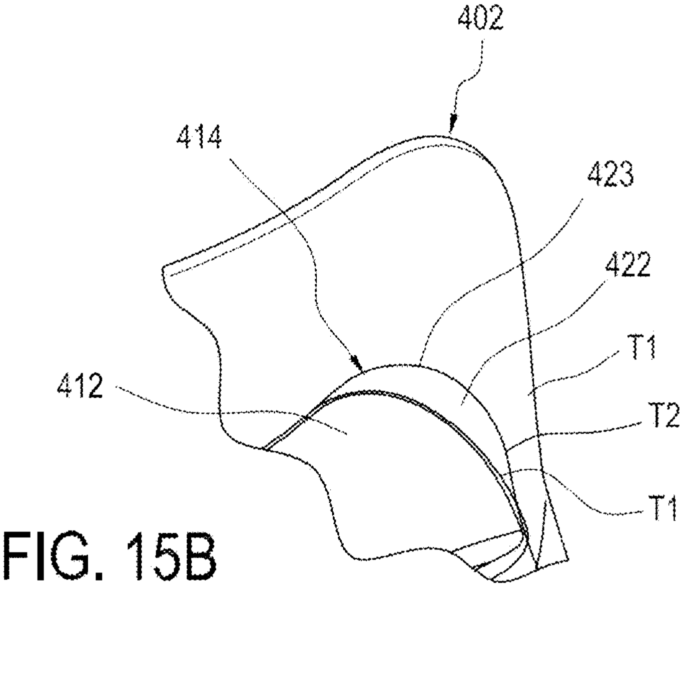
FIG. 15B is a detail view taken from detail XV B in FIG. 15A.
Figure 15C:
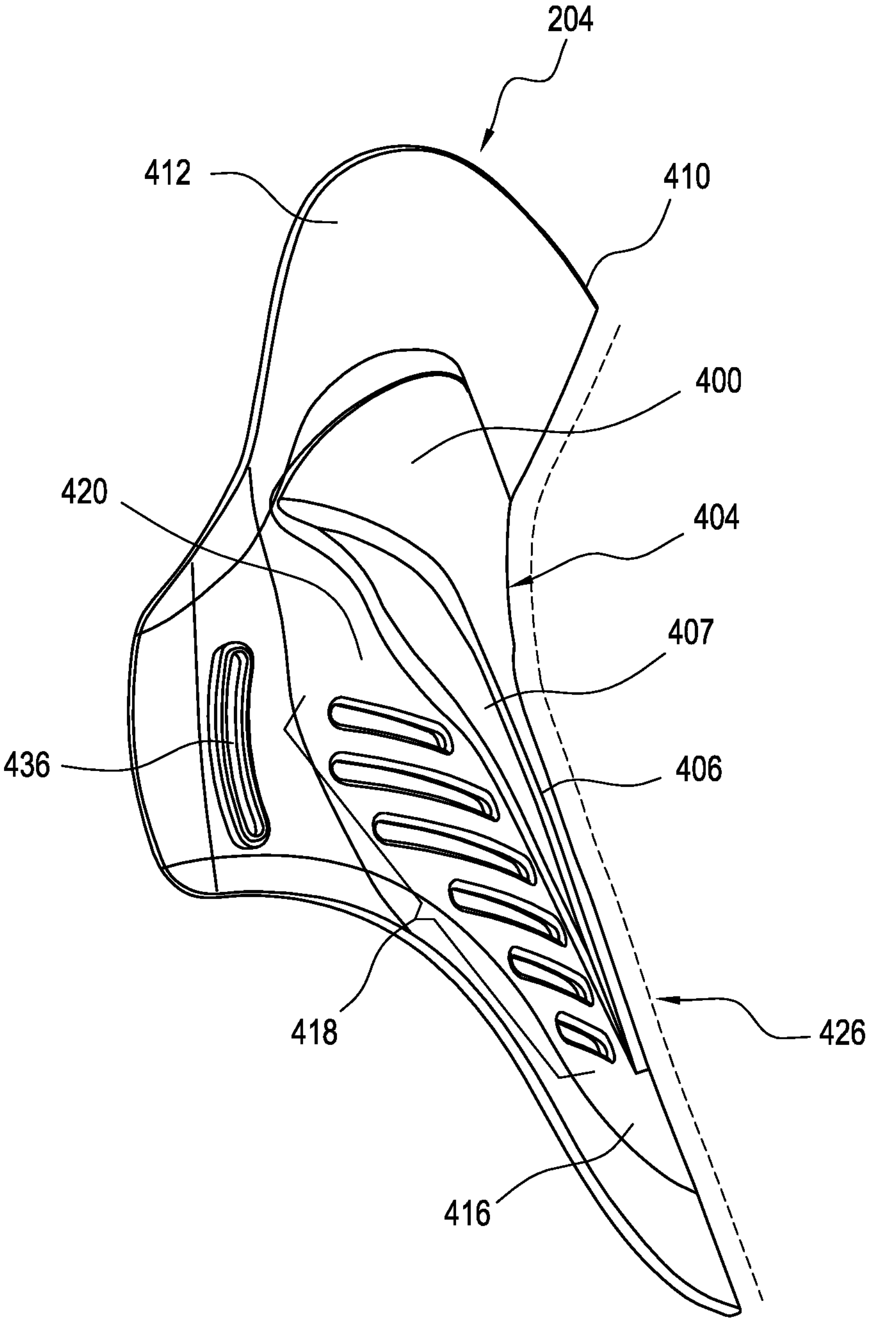
FIG. 15C is a side elevational view of the posterior component of FIG. 15A.

FIGS. 15A-15C depict an embodiment of the posterior component 204, particularly from the perspective of outside of the posterior component 204.

Figure 15D:
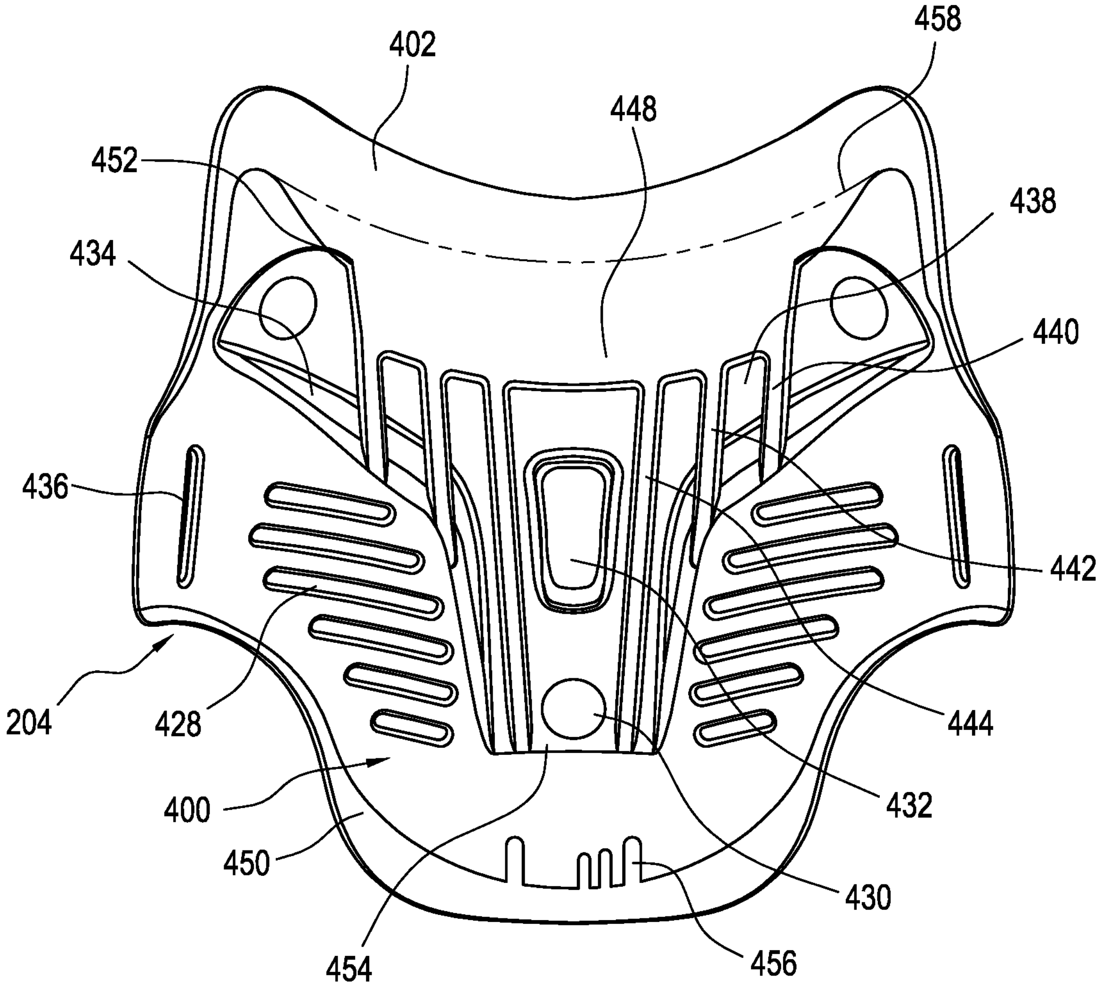
FIG. 15D is an elevational view of the posterior component in FIG. 15A showing an inner side.
Figure 15E:
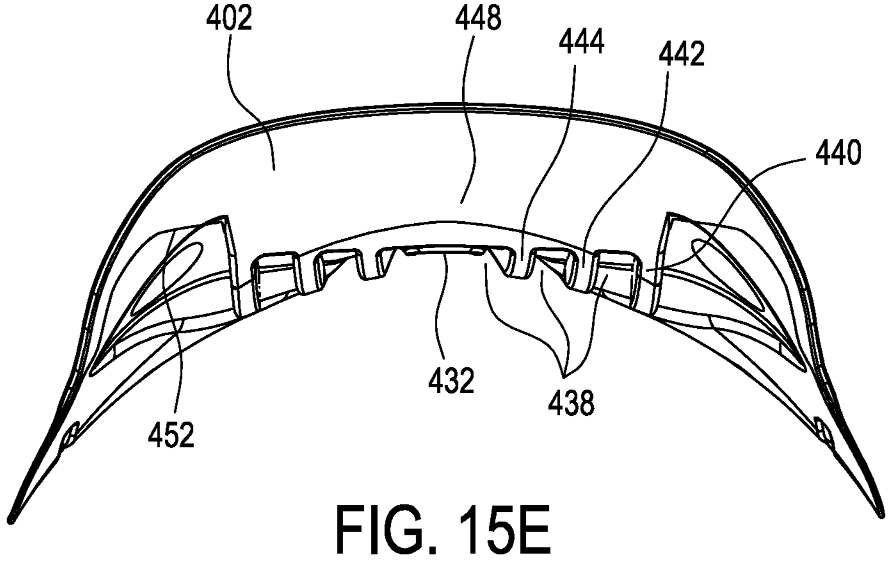
FIG. 15E is a top plan view of the posterior component of FIG. 15A.

The posterior component 204 includes a main part 400 and a flexible portion 402. It will be noted that FIG. 15A shows an outer side of the posterior component 204 that is intended to face away from the user whereas FIGS. 15D and 15E show the inner side of the posterior component 204 arranged to be placed adjacent to the user. From the outer side of the posterior component 204, the main part 400 defines a central convex portion or rib 404, whereas the rib 404 is concave on the inner side of the posterior component, protruding from a base section 424 of the main part 400 toward a top section 415 of the main part 400 to accommodate and apply pressure outside of the cervical spine. The top section 415 of the main part 400 extends continuously between first and second corners of the main part 400.

The depicted embodiment exemplifies how the main part 400 includes resilient or flexible portions forming the flexible portion 402 formed along the peripheral edges of the main part 400. In this embodiment, the main part 400 and the flexible portion 402 are formed by discretely different materials, wherein the main part 400 is formed from a more structurally rigid material, and the flexible portion 402 is formed from a material more resilient and flexible than the material forming the main part 400; for example, by overmolding a resilient or compliant material thereon. The use of flexible portions 402 allows the cervical collar 200 to distribute pressure peaks over larger areas in order to avoid the formation of pressure ulcers. The flexible portions 402 can also prevent pressure peaks even when the collar 200 is improperly applied.

The flexible portions 402 in the embodiment are continuous in that there are no breaks along the flexible portion 402 about the periphery of the main part 400. This is in contradistinction to flexible portions that comprise thinned portions forming tabs from the main part 400 that are sequentially provided along a periphery of the main part 400, and include clearances between each of the tabs to increase their flexibility. An advantage to the continuously formed flexible portion 402 is that there is an even distribution of pressure as opposed to individual and spaced tabs that are required to bear and exert pressure. It will be understood, however, that the continuously extending flexible portions 402 are provided by example, and the disclosure is not limited to the flexible portion 402 being continuous. Although the continuously extending flexible portions 402 embodiment is advantageous, discretely separated tabs or flexible areas may be provided in combination with the embodiments of this disclosure.

The main part 400 defines a convex rib 404, from the perspective of the outer side, that generally runs along a central axis C-C of the posterior component 204. Side sections 406 flare and curve from sides of the rib 404 and toward side extensions 405, as discussed above, to terminate at first and second corners of the main part 400. The side sections 406 form a Y-feature 408 with the rib 404 and the side extensions 405. The Y-feature 408 flares upwardly vertically along the cervical spine, and the side sections 406 have a curvature to provide improved anterior-posterior and lateral occipital support.

A series of slots 418 extends along the side extensions 405 from the lower section 460 located beneath the rib 404, and the slots 418 may be formed as shown above. However, additional slots that may not be sufficiently sized for receiving a strap may be formed and progressively diminish in size as the series of slots 418 approaches the rib 404. In this manner the side extensions 405 become more rigid as they draw toward the rib 404, thereby being less flexible and contributing to greater rigidity along the rib 404, which in turn corresponds to a user's cervical spine. The series of slots 418 sized for receiving straps may provide ventilation and compliance to the anterior component 236 and due to tensioning of the straps.

The series of slots 418 and their corresponding pattern provide flexibility to allow the posterior component 204 to conform and fit around the necks of varying anatomical sizes. The pattern of the series of slots 418 allow the posterior component 204 to be flexible where needed, such as along the side extensions 232 that overlap or are proximate to the anterior component 236, while remaining rigid in the necessary anterior-posterior and lateral directions, particularly along the axis C-C corresponding to the user's cervical spine.

The Y-feature 408 is in combination with the side sections 406 that form recesses 407, which extend to the series of slots 418 on each lateral side of the posterior component 204, created as a result of the Y-feature 408 protruding from the outer side. The recesses 407 transition in depth between the ends of the side sections 406, wherein the greatest depth of the recesses 407 is located between the ends of the side sections 406. The recesses 407 on the opposed sides of the rib 404 and contours of the side sections 406 form a pocket 420 for the anterior component 236 to nest into the posterior component 204 when it is secured therewith. The pocket 420 may enable the posterior component 204 to overlap the anterior component 236, and the pocket 420 reduces pressure of the anterior component 236 pushing into the neck of the user.

The flexible portion 402 is preferably provided around the periphery of the main part 400, and offers reduced edge pressure about the posterior neck and occiput of the user. The flexible portion 402 may be increased in designated areas to provide enhanced pressure relieving characteristics to the user. For example, there may be an increase in size of the flexible portion 402 from a border of the side extensions 405 to the upper sections 412 that extend on opposed sides of a peripheral recessed section 410 adapted to accommodate a user's occipital region.

The peripheral recessed section 410 may have a first flexible portion region 411 that has a width W1 that is greater compared to other areas and corresponding widths (collectively the second flexible portion region W2) of the flexible portion 402 about the periphery of the main part 400. The width W1 at the first flexible portion area 411 is provided at least in part to provide increased comfort to the user around the occipital bone and posterior neck, as shown by the vertical and horizontal directional arrows A, B within the first flexible portion area 411, by the yielding of the first flexible portion area 411 in the recessed section 410. The width of the first flexible portion area 411 may be variable from the upper sections 412 to the nadir of the peripheral recessed section 410 along the center line C-C. The second flexible portion region W2 may be variable in width depending on the location along the periphery of the main part 400, or may be uniform.

The upper sections 412 are anatomically shaped flared sections spaced apart by the concave and curved shaped recessed section 410, and a flexible portion of the upper sections 412 is shaped to correspond to and support an occipital region of a user of the collar 200. The upper sections 412 are arranged to gently cradle the side areas of a user's occiput so as not to place undue pressure on the cervical spine of the user. The contour of the recessed section 410 and the gradual rising of the flexible edge 402 between the upper sections 412 and the recessed section 410 provide increased comfort to the user around the occipital bone and posterior neck.

The main part 400 may be thinned at least at the upper sections 412 in that the main part 400 has a general thickness T1, and the thickness at the upper sections 412 has a gradual reduction or tapered thickness T2 from the general thickness T1 to a tip 423 of the upper sections 412. The tapered thickness T2 results in a thinned section 422 creating a three tiered range of flexure 414: flexure of the main part at the general thickness T1, flexure at the tapered thickness T2 of the main part 400 at the upper sections 412, and flexure at the flexible portion of the upper sections 412.

The thinned section 422 is covered and/or overmolded by material forming the flexible portion 402, wherein the amount of material forming the flexible portion 402 gradually increases as the thinned section 422 tapers to nothing and the material fully becomes the flexible portion 402 about the periphery or edge of the tip 423 of the thinned section 422. According to an embodiment, the combined thickness of the thinned section 422 and the material of the flexible portion 402 is generally the same as the general thickness T1. The flexible portion 402 may likewise have a same thickness as the general thickness T1.

As shown in FIG. 15C, the posterior component 204 defines a contoured profile having a general curvature 426 between the recessed section 410 and the base section 424 oppositely disposed relative to the recessed section 410 along the axis C-C. In this manner, pressure is applied to the upper sections 412 and the base section 424 to provide improved anterior-posterior and lateral support, and easing such pressure by the curvature which better corresponds to the anatomical relationship between the occiput and the shoulders of a user. The general curvature thus advantageously provides an improvement over existing cervical collars by providing enhanced support corresponding to a user's needs, as compared to exiting collars which primarily provide flat posterior portions that result in undesirable pressure points and discomfort.

FIGS. 15D and 15E exemplify an inner side to an alternative embodiment of the posterior component 204 intended to face a user. Fastener tabs 430 are provided at convenient locations to assure a firm grip to a liner of the posterior component 204. The posterior component 204 has a posterior opening 432 intended to be located generally along a cervical column of a user to provide pressure relief and ventilation to the posterior component 204 along the rear rib 404. The rear rib 404 is generally convex on the outer side of the posterior component 204, and is generally concave along the inner side of the posterior component 204. The concave inner side of the rear rib 404 serves to relieve pressure against the cervical column of a user, as evidenced by the recessed portions 434 generally corresponding to the Y-feature 408 which is on the outer side of the posterior component 204. Strap slots 436 are provided at side portions of the posterior component 204, and are oriented differently from the ventilation openings 428.

The flexible portion 402 extends along the main part 400 a greater distance along the inner side than the outer side, as evidenced by the boundary 458 corresponding to the extent to which the flexible portion 402 extends along the main part 400 on the outer side. The flexible portion 402 extends longer on the main part 400 and offers greater cushioning due in part to the material forming the flexible portion 402 being preferably softer and more compliant than the material forming the main part 400. For example, the flexible portion 402 material defines an upper flexible portion 448 extending longer than the flexible portion 402 on the outer side (past the boundary 458) so as to offer more cushioning along the inner side that corresponds to the occiput of the user, particularly since there may be substantial pressure exerted on the collar 200 by the user at this location. Within the cavity 438 formed by the Y-feature 408, the flexible portion 402 forms ribs 440, 442, 444 descending into the cavity 438 and generally extending along the curvature 426.

The ribs 440, 442, 444 are provided to reinforce the curvature 426 along the inner side of the posterior component 204, and better assure proper positioning of the user's neck. As the ribs 440, 442, 444 generally align with the curvature, they offer vertical stiffness to the posterior component 204 and track along the curvature 426. The ribs 440, 442, 444 are spaced from one another forming clearances 446 from one another to avoid pressure points, and to facilitate breathability of the posterior component 204. As the material forming the flexible portion 402 is more compliant, or softer than the material forming the main part 400, the ribs 440, 442, 444 may be trimmable depending on patient anatomy. For example, if the user's neck is substantially straight, some material may be removed from the ribs 440, 442, 444 to make the curvature less severe. This allows the posterior component 204 to be customizable based on individual patients' dimensions, a feature not provided by existing collar designs.

The Y-feature 408 gradually transitions along the inner side between upper transition 452 and lower transition 454 so that the concavity along the inner side is formed gradually to avoid any pressure points. Either the main part 400 may form such transitions, or the main part 400 may form the transitions in combination with the flexible portion 402 material, as similarly taught in regard to the outer side. The material forming the flexible portion 402 extends along a lower portion 450, and extends into at least one peripheral recess 456 formed by the main part 400, to better interlock the flexible portion 402 to the main part 400.

Figure 16A:
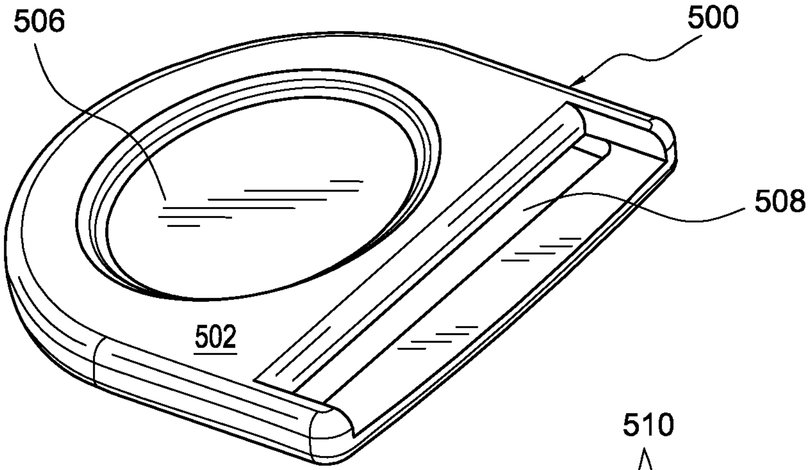
FIG. 16A is a perspective view of a first side of a strap tab.
Figure 16B:
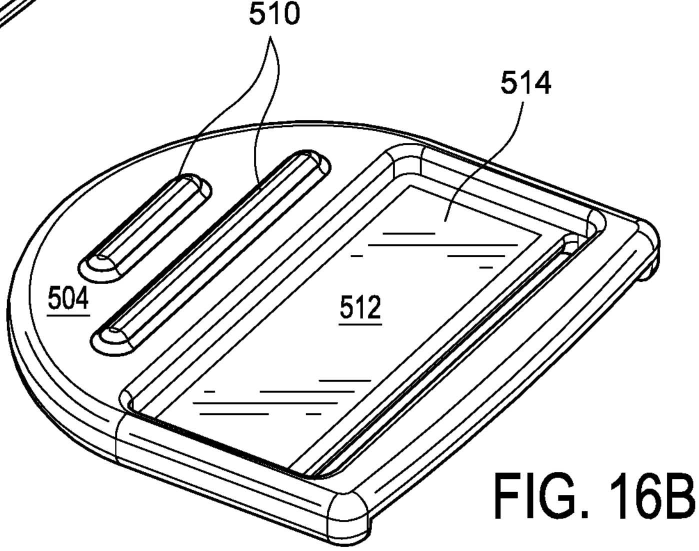
FIG. 16B is a perspective view of a second side of the strap tab of FIG. 16A.
Figure 16C:
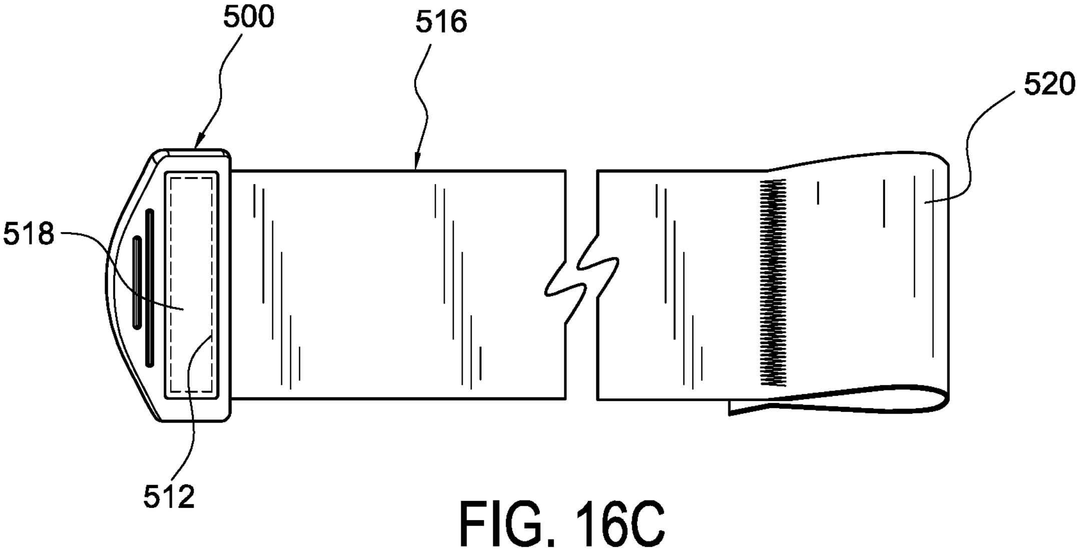
FIG. 16C is a plan view of a strap system.

FIGS. 16A-16C exemplify improved strap arrangements or systems for connecting the anterior and posterior components 202, 204. A strap tab 500 has a first surface 502 defining a recess 506 for improved gripping of the strap tab 500, and a second surface 504 having traction elements 510 for gripping. A slot 508 is formed for receiving a strap. The strap tab 500 forms a recess 512 for receiving an end portion 518 of a strap 516, as further illustrated in FIG. 16C. The recess 512 enables the end portion 518 of the strap 516 to lie flush in the strap tab 500, so the end portion 518 is confined within the peripheries of the first and second surfaces 502, 504, without protruding therefrom. This arrangement is provided to maintain the strap tab 500 in a low profile configuration so as not to significantly protrude from the anterior component 202. Suitable fasteners 514, such as hook material or hook formed by the strap tab 500 itself, may be located within the recess 512 to removably secure to the end portion 518. A second end portion 520 of the strap 516 may form a loop for engaging the strap on the posterior component.

Figure 17A:
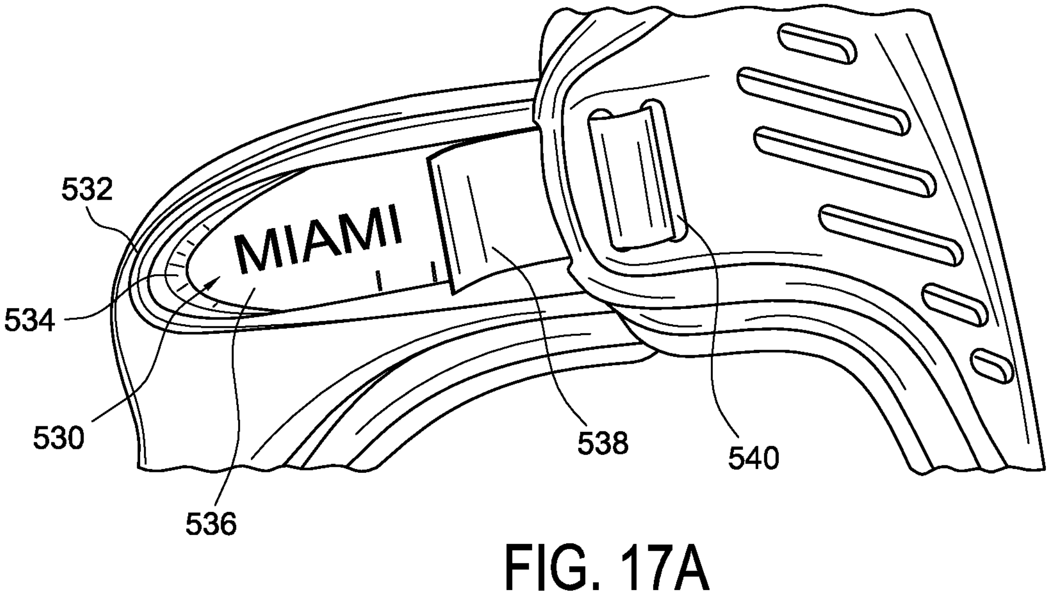
FIG. 17A is a schematic view of another embodiment of a strap system on the cervical collar of FIG. 2.

FIG. 17A exemplifies another strap arrangement or system. The strap 530 carries a grip 534 on a first end of the strap 530 that is adapted to correspond in geometry to a landing area 532 of the forward projections of the anterior component 202. A strap body 536 extends to the posterior component 204 from the grip 534 so that a second end 538 loops about a strap slot 540 of the posterior component 204. The second end 538 may be cinched about the posterior component, or include further means for securing, such as having corresponding hook and loop fastener to secure itself to the strap body 536. This arrangement advantageously prevents damage or inadvertent tampering with the straps due to accidental contact with the strap or the strap catching on an object, as the strap end is secured flush against the strap body 536. Additionally, this embodiment allows for a strap system to be repeatedly donned and removed without adjusting the length of the strap 530 each time, thereby enhancing convenience for a user especially over long-term use when the collar is worn more intermittently.

Figure 17B:
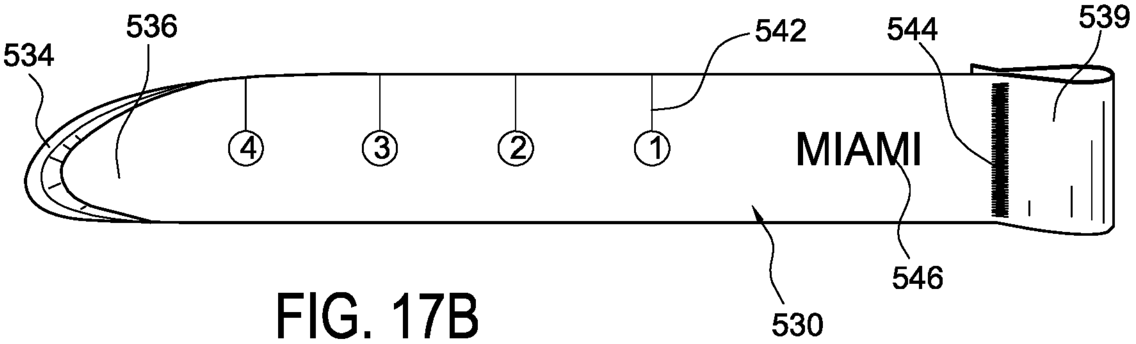
FIG. 17B is a plan view of a variation of the strap system of FIG. 17A.

FIG. 17B shows how the strap 530 may include a scale 542 printed thereon for determining sizing of the strap 530, and may further include logos or other information 546 printed thereon. In the variation of FIG. 17B, second end 539 of strap 530 defines a loop and is permanently stitched by stitching 544 to maintain its shape. In this embodiment, the loop is permanently secured to the posterior component 204 so that the strap 530 is not adjustable from the posterior component 204, but rather is only adjustable by pulling from a first end at the anterior component 202. However, the grip 534 may be removable (as opposed to being permanently disposed on the strap 530—thereby only being removed by destroying or significantly modifying the strap 530) from the strap 530, such that the strap 530 can be trimmed from a first end, and the grip 534 can be subsequently secured once the strap 530 is resized. Any suitable arrangement may be provided to removably attach the grip 534 to the strap 530, such as by a clamshell arrangement, adhesives, hook and loop fastener, or any other suitable arrangement.

Figure 17C:
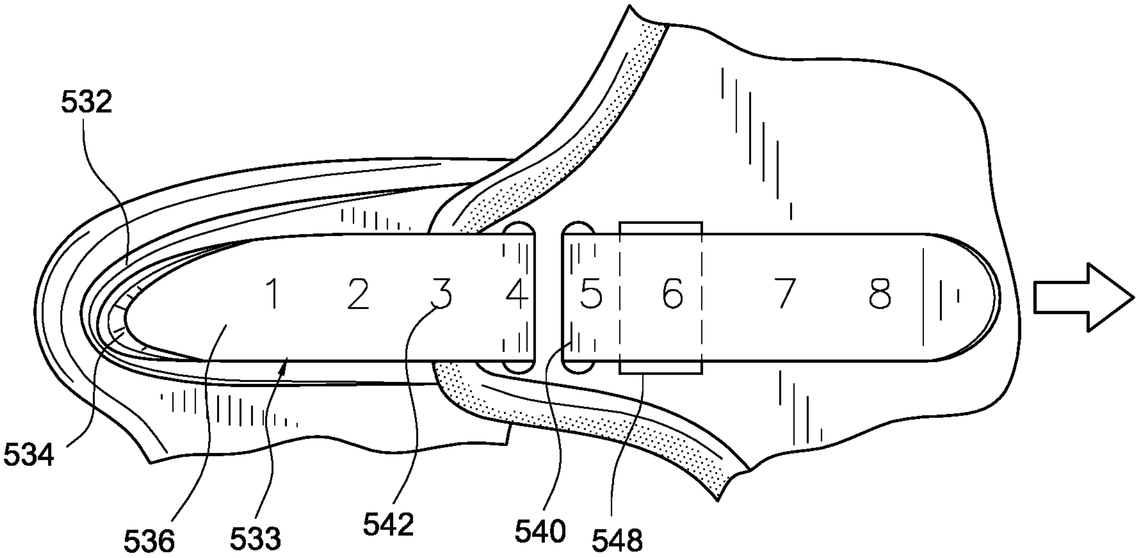
FIG. 17C is a schematic view of yet another embodiment of a strap system on a cervical collar.

FIG. 17C illustrates another embodiment whereby strap 533 passes through and over a strap slot 540 and secures internally to the posterior component 204. In this embodiment, an outer surface of the strap 533 may have a hook-receivable surface, and the posterior component 204 can include a corresponding fastener 548 that engages the hook-receivable surface. The strap 533 includes indicia 542 that peer through an opening of the strap slot 540 to show the extent or length the strap 533 is tensioned. This arrangement advantageously prevents damage, as discussed above, by maintaining the strap 533 in close proximity to or flush against the cervical collar 200, while still providing indicia for convenient and accurate sizing of the collar 200 to accommodate individual users' dimensions.

The disclosed embodiments of an orthopedic device, such as a cervical collar, having anterior and posterior components that are positioned about anatomy of a user such as the neck, to conform thereto and provide support, immobilization, and stabilization thereto, provide improvements that allow a single cervical collar to be applied for treatment to a wide variety of patients having varying sizes or degrees of swelling of anatomical portions.

It is understood that while the disclosed embodiments are designed to accommodate users having different sized anatomies, the size of the disclosed embodiments and the components thereof can be adjusted so different users having different sized anatomical portions may benefit from the present designs.

It is understood that while the disclosed embodiments of the cervical collar are shown having discrete anterior and posterior components, the anterior and posterior portions may be connected to each other along one side thereof, and a single strap or circumferential adjustment mechanism can be provided between the anterior and posterior component along the other side thereof.

It will also be recognized that the flexible portions, and the living hinge and slot structures, can be provided to a collar, without providing other features, such as the height adjustability, to the collar.

It is to be understood that not necessarily all objects or advantages may be achieved under any of the particular embodiments. For example, those skilled in the art will recognize that the embodiments may be embodied or carried out in a manner that achieves or optimizes one advantage or group of advantages as taught without achieving other objects or advantages as taught or suggested herein.

The skilled artisan will recognize the interchangeability of various disclosed features from the different embodiments. Besides the variations described herein, other known equivalents for each feature can be mixed and matched by one of ordinary skill in this art to construct an orthopedic device under principles of the disclosed embodiments.

Although this disclosure is in the context of certain exemplary embodiments and examples, it therefore will be understood by those skilled in the art that the disclosure extends beyond the specifically disclosed embodiments to other alternative embodiments and/or uses of the embodiments, and obvious modifications and equivalents thereof. It is intended that the scope of the present disclosure should not be limited by the particular disclosed embodiments described above.

The invention claimed is:

1. A posterior component for a cervical collar, comprising:

a rigid main part formed from a structurally rigid, unfolding material;

the rigid main part defining a base section, and a rear rib extending vertically, elongate, and centered on a central axis of the posterior component, the rear rib being convex along an outer side of the posterior component and concave along an inner side of the posterior component, an outer side of the rigid main part defining first and second side sections extending from opposed first and second sides of the rear rib;

wherein the first and second side sections and the rear rib forms a Y-feature, the first and second side sections flare upward vertically away from the rear rib and the central axis of the posterior component to a top section of the rigid main part, such that the first and second side sections extend away from the central axis;

wherein the rear rib protrudes outwardly from the base section relative to a lower section and side extensions of the rigid main part and extends to the top section forming a top periphery shared by the outer side of the rigid main part and the Y-feature, the top section extends continuously between first and second corners of the rigid main part where the first and second side sections terminate, respectively;

wherein the Y-feature, in combination with the first and second side sections, forms recesses extending to a series of slots on each lateral side of the posterior component, the recesses being formed by the Y-feature protruding from the outer side of the posterior component relative to the lower section and the side extensions;

wherein the recesses progressively transition in depth relative to the lower section and the side extensions and toward the first and second corners of the rigid main part, respectively, as the first and second side sections extend away from the central axis.

2. The posterior component of claim 1, further comprising a flexible portion provided about a periphery of the rigid main part, the flexible portion being formed from a resilient material and more flexible than the rigid main part.

3. The posterior component of claim 2, wherein the flexible portion defines a peripheral recessed section extending and varying in width between first and second upper sections of the rigid main part, the rigid main part forming a top peripheral recess relative to the central axis and coextensive to the peripheral recessed section of the flexible portion.

4. The posterior component of claim 3, wherein a width of the flexible portion between the first and second upper sections has a greatest width along the central axis of the posterior component.

5. The posterior component of claim 3, wherein the peripheral recessed section has a nadir between the first and second upper sections of the rigid main part along the central axis of the posterior component.

6. The posterior component of claim 3, wherein the top peripheral recess of the rigid main part varies in depth relative to the peripheral recessed section of the flexible portion between the first and second upper sections.

7. The posterior component of claim 1, wherein a flexible portion extends along a periphery o the rigid main part, and extends over an inner side of the top section of the rigid main part toward the base section more than it extends over an outer side.

8. The posterior component of claim 7, wherein the flexible portion forms at least one interior rib extending from the top section and over the rigid main part within a cavity formed by the rear rib and side extensions on the inner side of the posterior component.

9. The posterior component of claim 8, wherein the at least one interior rib taperstapering in thickness from the top section to the base section according to a tapering depth of a concavity of the rear rib on the inner side.

10. The posterior component of claim 8, wherein the at least one interior rib includes first and second sets of interior ribs on first and second sides of a central axis of the posterior component, the first and second sets of interior ribs each including at least two interior ribs having different heights according to an extent the at least two interior ribs extend relative to a concavity of the rear rib and the side extensions of the posterior component.

11. The posterior component of claim 2, wherein the rigid main part has a base thickness, and a thickness at first and second upper sections that has a gradual reduction in thickness from the base thickness to a tip of the first and second upper sections.

12. The posterior component of claim 11, wherein the flexible portion extends from the rigid main part at the first and second upper sections and has a thickness that varies according to the thickness of the first and second upper sections.

13. The posterior component of claim 1, wherein the top section has a curved shaped recess between the first and second corners.

14. The posterior component of claim 13, wherein a curvature is defined between the top section and the rear rib when viewed from a side elevational view, wherein the rear rib is elongate when viewed from a rear elevational view.

15. The posterior component of claim 1, wherein the rigid main part defines a vertically elongate posterior opening centered on the central axis and the rear rib extending on opposed sides of the vertically elongate posterior opening along the central axis, the first and second side sections extending away from the central axis at a location of the central axis corresponding to an upper section of the vertically elongate posterior opening, the vertically elongate posterior opening being entirely confined within the rear rib and extending through the rigid main part, the top section extending above the vertically elongate posterior opening.

16. The posterior component of claim 1, wherein the rigid main part defines a single continuous arcuate peripheral edge formed by the rear rib and the first and second side sections at the top section of the rigid main part.

17. The posterior component of claim 1, wherein the posterior component defines a contoured profile having a curvature between the top section and the base section oppositely disposed relative to one another along the central axis of the posterior component.

18. The posterior component of claim 1, wherein the rigid main part defines first and second upper sections formed as flared sections spaced apart by a concave and curved shaped recessed section.

19. The posterior component of claim 1, wherein a depth of the recesses has a greatest depth located between the first and second corners of the rigid main part, where the first and second side sections terminate, respectively, and first and second corners of the base section, where the first and second side sections begin, respectively.

* * * * *